United States Patent
Meurs et al.

(10) Patent No.: US 7,442,509 B2
(45) Date of Patent: Oct. 28, 2008

(54) DETECTING MUTATIONS IN THE FELINE CARDIAC MYOSIN BINDING PROTEIN C GENE ASSOCIATED WITH HYPERTROPHIC CARDIOMYOPATHY IN CATS

(75) Inventors: Kathryn Meurs, Viola, ID (US); Mark Kittleson, Davis, CA (US)

(73) Assignees: The Ohio State University Research Foundation, Columbus, OH (US); University of California, Davis, Davis, CA (US)

( * ) Notice: Subject to any disclaimer, the term of this patent is extended or adjusted under 35 U.S.C. 154(b) by 0 days.

(21) Appl. No.: 11/445,421

(22) Filed: Jun. 1, 2006

(65) Prior Publication Data

US 2007/0087359 A1    Apr. 19, 2007

Related U.S. Application Data

(60) Provisional application No. 60/686,647, filed on Jun. 1, 2005.

(51) Int. Cl.
*C07H 21/04* (2006.01)
*C12Q 1/68* (2006.01)

(52) U.S. Cl. .......................... 435/6; 435/91.1; 435/91.2

(58) Field of Classification Search ........................ None
See application file for complete search history.

(56) References Cited

U.S. PATENT DOCUMENTS

| 5,912,121 | A   | 6/1999 | Seidman et al. | |
| 2003/0092019 | A1* | 5/2003 | Meyer et al. | 435/6 |
| 2004/0086876 | A1  | 5/2004 | Seidman et al. | |

OTHER PUBLICATIONS

Meurs et al. Genomics, vol. 90, pp. 261-264, 2007.*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Tacher et al. (J. of Heredity, vol. 96, No. 7, pp. 812-816, 2005).*
http://www.indys.org.uk/hcm.htm., Feb. 14, 2008.*
Fananapazir et al., "Genotype-Phenotype Correlations in Hypertrophic Cardiomyopathy: Insights Provided by Comparisons of Kindreds With Distinct and Identical beta-Myosin Heavy Chain Gene Mutations," Circulation. vol. 89, No. 1, Jan. 1994, pp. 22-32.
Kittleson et al., "Familial Hypertrophic Cardiomyopathy in Maine Coon Cats: An Animal Model of Human Disease," Circulation, vol. 99, No. 24, Jun. 22, 1999, pp. 3172-3180.
Meurs et al., "A cardiac myosin binding protein C mutation in the Maine Coon cat with familial hypertrophic cardiomyopathy," Human Molecular Genetics, (2005), vol. 14, No. 23, pp. 3587-3593.
Moolman et al., "A Newly Created Splice Donor Site in Exon 25 of the MyBP-C Gene Is Responsible for Inherited Hypertrophic Cardiomyopathy With Incomplete Disease Penetrance," Circulation, vol. 101, No. 12, Mar. 28, 2000, pp. 1396-1402.
Reiser et al., "Electrophoretic separation and quantitation of cardiac myosin heavy chain isoforms in eight mammalian species," Am J Physiol, vol. 274, No. (3 Pt 2), Mar. 1998, pp. H1048-H1053.
Richard et al., "Hypertrophic Cardiomyopathy: Distribution of Disease Genes, Spectrum of Mutations, and Implications for a Molecular Diagnosis Strategy," Circulation, vol. 107, No. 17, May 6, 2003, pp. 2227-2232.
Watkins et al., "Expression and Functional Assessment of a Truncated Cardiac Troponin T That Causes Hypertrophic Cardiomyopathy," J. Clin. Invest., vol. 98, No. 11. Dec. 1996, pp. 2456-2461.
Winegrad, "Cardiac Myosin Binding Protein C," Circulation Research, vol. 84, No. 10, May 28, 1999, pp. 1117-1126.
Winegrad, "Myosin Binding Protein C, a Potential Regulator of Cardiac Contractility," Circulation Research, vol. 86, No. 1, Jan. 7-21, 2000, pp. 6-7.
Witt et al., "Hypercontractile Properties of Cardiac Muscle Fibers in a Knock-in Mouse Model of Cardiac Myosin-binding Protein-C," J Biol Chem., vol. 276, No. 7, Feb. 16, 2001, pp. 5353-5359.

* cited by examiner

*Primary Examiner*—Jeanine A Goldberg
(74) *Attorney, Agent, or Firm*—Calfee, Halter & Griswold LLP

(57) ABSTRACT

The invention pertains to methods for detecting the presence or absence of a mutation associated with hypertrophic cardiomyopathy in cats, particularly domesticated cats, and more particularly Maine Coon cats. The methods include detecting the presence or absence of a mutation in the feline MYBPC gene, and identifying feline subjects that have or are at risk of developing hypertrophic cardiomyopathy.

9 Claims, 23 Drawing Sheets

Unaffected

GTGTTCGAG[GCC]GAGACAGACG

Affected

GTGTTCGAG[CCC]GAGACAGACG

EXON 3 (SEQ ID NO: 3)

TCTCAGCCTTTAGCAAGAAGCCAAGGTCAGTGGAAGTGGCAGCCAGCAGCTCTGCTGTGTTCGAGGCC
GAGACAGAGCGGTCAGGAGTAAAGGTGCGCTGGCAGCGGGGGGGCAGTGACATCAGCGCCAGTGACAAGTATGGCCT
AGCAGCCGAGGGCACTGAGGCACACTCTGACAGTGCGGGACGTGGGCCCCACCGACCAGGGACCCTACGCAGTCATC
GCTGGCTCCTCCAAGGTCAAGTTTGACCTCAAGGTCATAGAAGCAG

Exon 3 (SEQ ID No: 4)
agtggaagtggcagccagcagctctgctgtgttcgagg<u>cc</u>gagacagagcggtcaggagt
aaaggtgcgctggcagcnnnnnnnncagtgacatcagcgccagtgacaagtatggcctagc
agccgagggcactgaggcacactctgacagtgcgggacgtgggccccaccgaccagggac
cctacgcagtcatcgctggctcctccaaggtcaagtttgacctcaaggt

Exon 4 (SEQ ID No : 5)
tctcagcctttagcaagaagccaaggtcagtggaagtggcagccagcagctctgctgtgttcgaggccgagacagag
cggtcaggagt
aaaggtgcgctggcagcggggggggcagtgacatcagcgccagtgacaagtatggcctagc
agccgagggcactgaggcacactctgacagtgcgggacgtgggccccaccgaccagggac
cctacgcagtcatcgctggctcctccaaggtcaagtttgacctcaaggt
catagaagcag

Intron 4 (SEQ ID No : 6)
Gtaagaccctggtccgccttccct-aggtttga
gcttct------ggggcagcctggccatctctccct-cacccagggtataggaggagcct
ttccactgtctcgcctttgctttggctgagccgtctgccaggaattcccttcctcccttt
tctgcagcaagacctcactgagtgtccccatgtgtctccctggcctgttccagtcat
ccagggtataggaggagccttttccactgtctcgcctttgctttggctgagccgtctgcca
ggaattcccttcctccttttctgcagcaagacctcactgagtgtccccatgtgtctccc
tggcctgttccagtcat

Exon 5 (SEQ ID No: 7)
agagaaggcagagcctgtgccgggccctgctcctgcccctactgaggctcctggaggctccggagaagcactgacct
cgaccactgaggaggaaggaggctccccaagtcccaaag

Intron 5-6
Gtgag

Exon 6 (SEQ ID No: 8)
gtcaagttcagcagcccccgatggctctggtgcct
ctgatgaccccatcggcctctttgtgatgcggccacaggatggcgaggtgaccgtgg

Exon 7 (SEQ ID No: 9)
gtggctgcatcaccttctcagcccgcgtggccggcgccagcctcctgaaaccgcccacagtcaagtggttcaagggc
aagtgggtggacctga     gcagcaaggtgggccaacacctgcagctgcacaacagttacgaccggaccagcaag ggtggacctgagcagcaaggtgggccaacacctgcagctgcacaacagttacgaccggaccagcaaggt
accttgctggtc
cggtcgtaactgttgtgcagctgcaggtgttggcccaccttgctgctc
aggtccacccacttgcccttgaaccacttgactgtgggcggtttcaggaggctggcgccg
gccacgcgggctgagaaggtgatg

Exon 8 (SEQ ID No: 10)
gtctacctgtttgagctgcacattacagatgcccagactactttcgcaggtggctac
cgctgtgaggtttccaccaaggacaaatttgacagctgcaacttcagtctcactgtccatg

Figure 9 continued

Intron 8-9   (SEQ ID No: 11)
gtgagggagccctgg----cgtcctgggctcagg-tccccatgggtcttatcc
cccacgtctgcctccatttcccaacactaaggaggatgtctagtcccaacaggaca--ac cgctgcccacatgcccagtgctgctcatgcaggg
ggaaaggctcagaatgtggggtcctggggcagatgcccctctca-agggtcatggatgg
gcaggtctgt tgaacgcagag

Exon 9 (SEQ ID No: 12)
Gccgttggccctggagacctggacctccgatcagctttccgccgcac

Intron 9   (SEQ ID No: 13)
gt
gagtggtcatctcttctcagggacggcggggaggccagtgctgggatctgaagcccctcg
gggtc

Exon 10   (SEQ ID No: 14)
gagcctggctggaagtggtcggcggatcag

Exon 11   (SEQ ID No: 15)
GTGACAGCCACGAGGACGCTGGA
ACTCTGGATTTCAGCTCGCTGCTGAAGAAGAG

Exon 12
AGA

Exon 13   (SEQ ID No: 16)
CAGTTTCCGGAACCTAAG

Exon 14   (SEQ ID No: 17)
ggacccgaggctggaggcgccagccgaggaggacgtgtgggagatcctgcggcaggca
tcccccctccgaatatgagcgcatcgccttccagcacggcatcaccgacctgcgtggcatg
ctcaagaggctcaagggcatgaagcgagatgagaagaag

Exon 15 (SEQ ID No: 18)
cctttcagaagaagctggagcccgc
ctaccaggtgagcaagggccacaagatccggctgaccgtggagctggccgaccccgacgc
cgaggtcaagtggctgaagaatggacaggagatccagatgagcggcag

Exon 16
caa

Exon 17   (SEQ ID No: 19)
gtacatcttcgagtccgtgggtgccaagcgcacnctgnaccatcanccagtgctcgctgagccgatgacgc
ggcctaccagtgcgtggtnnnnnnnnagaagtgcantaccgagctgttcgtcaaag

Exon 18   (SEQ ID No: 20)
agagccccccgtgctgatcactcggcccctggaagaccagctggtgatggtggggcagcg
ggtggagtttgagtgcgaagtgtctgaggaggggcccaggtcaagtgg

Exon 19   (SEQ ID No: 21)
ggctgaaggatggggtggagctgaccagggaggagaccttcaaataccggttcaagaagg
acgggcagagacaccacctcatcatcaactaggcgatcgctggaggacgcggggcactac
ncgctgcgcaccagcgggggccaggcgctggccgagctcatcgttcagg

Figure 9 continued

Exon 20  (SEQ ID No: 22)
aaaagaagctggaggtgtaccagagcatcgcagacctgaccgtgggtgcaaaggaccaggcggtg
ttcaagtgtgaagtgtccgatgagaacgtgcggggcgtgtggctgaagaacgggaaggag
ctggtgcccgacagccgcgtgaaggtgtcccacattgggcg

Exon 21  (SEQ ID No: 23)
agtccacaaactgaccattgacgacgtcacgcctgccgacgaggcggactacagctttgtg
cctgagggcttcgcctgcaacctgtcagcgaaactccatttcatgg

Exon 22  (SEQ ID No: 24)
gaggtcaagattgacttcgtgcccaggcaag

Exon 23  (SEQ ID No: 25)
agaacctcccaagatccacctggactgcccgggccgcaagccggataccattgtggttgt
ggctgggaacaagctacgcctggatgtccctatctctggggaccctgctcccactgtgat
ttggcagaaggctatcacgcag

Intron 23  (SEQ ID No: 26)
gtactgtggatccctcctccacttccccatctgtaaaatgggtg
tccaggctgagtcagcccctcttccccntgcttccctccggctctgt

Exon 24  (SEQ ID No: 27)
gaagaacaaggtcccagcagggccatccctggatgccccaggggggaggatgcaggtgacagtg
acgagtgggtgtttgacaagaag

Exon 25  (SEQ ID No: 28)
gctgctgtgtgagaccgagggccgggtgcgggtggagaccaccaaggaccgcagcatctt
cactgtcgaggggcagagaaggaagacgagggtgtctacgttgtcacggtgaagaaccc
cgtgggcgaggaccaggtcaacctcacagtcaaggtcatcg

Exon 26  (SEQ ID No: 29)
atgtgccagatcccccgcggccccaagatcagcaatgtgggtgaggactcctgcaccgtg
cagtgggagccgcctgcctacgacggggacagccagtcctggg

Exon 27  (SEQ ID No: 30)
ggctacatcctggagcgcaagaagaagaagagcttccggtggatgcggctgaactttgacctgctgcaggagctgag
ccacgaggcacggcgcatgattgagggcgtggtgtatgagatgcgagtc
tacgcggtcaatgccatcggcatgtccaggcccagccctgcctcccagcccttcatgcct
attg

Exon 28 (SEQ ID No: 31)
ggcccccccagtgagcccacccacctggccgtggaggatgtctcagacaccaccgtctccctcaagtggcggcc
cccggagcgggtgggagccggaggcttggatggctacagcgtggagtattgccgggaggg ctg

Exon 29  (SEQ ID No: 32)
gctcggagtgggtagctgccctggaggggctgacagaacgcacctcgttgctggtgaaggacctgcccacggggcc
cggctgctcttccgtgtgcgggcgcacaatatggcggggcccggggcccccatcgccaccaaggagcccgtgacggt
gcaggagatactgc

Exon 30  (SEQ ID No: 33)
gacggccacggctccaggtgccccggcacctgcgccagaccatccagaggaaggtcggggagcccgtgaacctcctc
attcctttccagg

Figure 9 continued

Exon 31 (SEQ ID No: 34)
cagggcaagccccggcctcaggtgacctggaccaaagaggggcagccactggcaggcgaggaggtgagcatccgcaa
cagccccacggacaccatcctgttcatcc
gggctgctcaccgcgcccactctggcacctacgaggtgatgctgcggatcgagaacatgg
aggacaaggccacgctggtcctgcgggtcgtt

Intron 31 (SEQ ID No: 35)
GGTGCGTGGCACTGGGGCCCCCTCTCTGAGATGCCCAGAGACCCTGC
AGAAGGTGGCAGGCCAGGTCCAGGCTGGCGGGGGTGAGGGGGCCTCCCAGGGCCCTCTGT
TCATACTCCAGCAGTCTCAGGAGGTCTGTTCCGGCTGGTCTCTCTCCTGCAG

Exon 32 (SEQ ID No: 36)
acaagccaagccctccccaggatattcgggtcactgaggcatgg
ggtttcaatgtggttctggagtggaagccaccccaggatgatggtaacacagagatcttg
ggttacacagtacagaaagccgacaagaagaccatgg

Exon 33 (SEQ ID No: 37)
gagtggttcaccgtcttggagcattaccgtcgcactcactgtgtcgtctcggg
agctcatcattgggcaacgggctactacttccggggtcttcagccataacacggtgggac
ccagtgacaacgcggccaccaccaaggagcctgtctttatccccagac          cag

Intron 33-34 (SEQ ID No: 38)
gtgct gtacctttactcccaccccc
gtgctgtacctttactcccaccccaggaggagctggggcagggaggcggtatgagcagggaggggc
Ctagcgtggtgtggcactcttggtgcaaagtcttatcacccacag

Exon 34 (SEQ ID No: 39)
gcatcacatatgagc
cacccaactacaaggccctggacttctccgagggcccgagcttcactcgccctctggtg
aaccgctcagtcattgct ggctacaatgctaccctctgctgtgctgtcgnggggtagcc ccaagg

Exon 35 (SEQ ID No: 40)
cat
cccaagatttcctggttcaagaatggcctggacctgggagaagatgcccgcttccgcatgttcagcaagcatggtgt
gtt/cgaccttggagatcagaaagacct
gcccctttgatggggcgtctatgtctgcagggccaccaacttacaaggcgaggcacagt
gtgagtgccgcctggaggtgcgag

Figure 10

Human MYBPC Gene

```
1: U91629. Reports Human cardiac myo...[gi:2920822]                    Links
LOCUS       HSU91629               24066 bp    DNA     linear   PRI 01-MAR-1998
DEFINITION  Human cardiac myosin binding protein-C (MyBP-C) gene, complete
            cds.
ACCESSION   U91629
VERSION     U91629.1  GI:2920822
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Euarchontoglires; Primates; Catarrhini;
            Hominidae; Homo.
REFERENCE   1  (bases 1 to 24066)
  AUTHORS   Niimura,H., Bachinski,L.L., Watkins,H., Thierfelder,L.,
            Chudely,A.E., Anastasakis,A., Toutouzas,P., Liew,J., McKenna,W.,
            Sole,M.J., Roberts,R., Seidman,J.G. and Seidman,C.E.
  TITLE     Direct Submission
  JOURNAL   Submitted (28-FEB-1997) Department of Genetics, Harvard Medical
            School, 200 Longwood Ave., Boston, MA 02115, USA
FEATURES             Location/Qualifiers
     source          1..24066
                     /organism="Homo sapiens"
                     /mol_type="genomic DNA"
                     /db_xref="taxon:9606"
                     /chromosome="11"
                     /map="11p11.2"
     gene            1011..22247
                     /gene="MyBP-C"
     mRNA            join(1011..1059,2177..2443,3067..3180,3569..3667,
                     3758..3906,5139..5256,5775..5823,6000..6029,6201..6254,
                     6651..6653,7036..7053,7310..7473,10025..10157,
                     10391..10393,10504..10628,10714..10819,10905..11071,
                     11493..11658,12406..12512,12618..12647,13860..13999,
                     14246..14326,14971..15130,15855..15959,16070..16258,
                     17638..17772,18440..18607,19638..19726,19896..20091,
                     20315..20454,20675..20834,20945..21081,21389..21575,
                     21766..21802,21931..22247)
                     /gene="MyBP-C"
                     /product="cardiac myosin binding protein-C"
     CDS             join(1035..1059,2177..2443,3067..3180,3569..3667,
                     3758..3906,5139..5256,5775..5823,6000..6029,6201..6254,
                     6651..6653,7036..7053,7310..7473,10025..10157,
                     10391..10393,10504..10628,10714..10819,10905..11071,
                     11493..11658,12406..12512,12618..12647,13860..13999,
                     14246..14326,14971..15130,15855..15959,16070..16258,
                     17638..17772,18440..18607,19638..19726,19896..20091,
                     20315..20454,20675..20834,20945..21081,21389..21575,
                     21766..21776)
```

Figure 10 continued

```
/gene="MyBP-C"
/codon_start=1
/product="cardiac myosin binding protein-C"
/protein_id="AAC04620.1"
/db_xref="GI:2920823"
```

(SEQ ID No: 41)
/translation="MPEPGKKPVSAFSKKPRSVEVAAGSPAVFEAETERAGVKVRWQR

GGSDISASNKYGLATEGTRHTLTVREVGPADQGSYAVIAGSSKVKFDLKVIEAEKAEP

MLAPAPAPAEATGAPGEAPAPAAELGESAPSPKGSSSAALNGPTPGAPDDPIGLFVMR

PQDGEVTVGGSITFSARVAGASLLKPPVVKWFKGKWVDLSSKVGQHLQLHDSYDRASK

VYLFELHITDAQPAFTGSYRCEVSTKDKFDCSNFNLTVHEAMGTGDLDLLSAFRRTSL

AGGGRRISDSHEDTGILDFSSLLKKRDSFRTPRDSKLEAPAEEDVWEILRQAPPSEYE

RIAFQYGVTDLRGMLKRLKGMRRDEKKSTAFQKKLEPAYQVSKGHKIRLTVELADHDA

EVKWLKNGQEIQMSGSKYIFESIGAKRTLTISQCSLADDAAYQCVVGGEKCSTELFVK

EPPVLITRPLEDQLVMVGQRVEFECEVSEEGAQVKWLKDGVELTREETFKYRFKKDGQ

RHHLIINEAMLEDAGHYALCTSGGQALAELIVQEKKLEVYQSIADLMVGAKDQAVFKC

EVSDENVRGVWLKNGKELVPDSRIKVSHIGRVHKLTIDDVTPADEADYSFVPEGFACN

LSAKLHFMEVKIDFVPRQEPPKIHLDCPGRIPDTIVVAGNKLRLDVPISGDPAPTVI

WQKAITQGNKAPARPAPDAPEDTGDSDEWVFDKKLLCETEGRVRVETTKDRSIFTVEG

AEKEDEGVYTVTVKNPVGEDQVNLTVKVIDVPDAPAAPKISNVGEDSCTVQWEPPAYD

GGQPILGYILERKKKKSYRWMRLNFDLIQELSHEARRMIEGVVYEMRVYAVNAIGMSR

PSPASQPFMPIGPPSEPTHLAVEDVSDTTVSLKWRPPERVGAGGLDGYSVEYCPEGCS

EWVAALQGLTEHTSILVKDLPTGARLLFRVAHNMAGPGAPVTTTEPVTVQEILQRPR

LQLPRHLRQTIQKKVGEPVNLLIPFQGKPRPQVTWTKEGQPLAGEEVSIRNSPTDTIL

FIRAARRVHSGTYQVTVRIENMEDKATLVLQVVDKPSPPQDLRVTDAWGLNVALEWKP

PQDVGNTELWGYTVQKADKKTMEWFTVLEHYRRTHCVVPELIIGNGYYFRVFSQNMVG

FSDRAATTKEPVFIPRPGITYEPPNYKALDFSEAPSFTQPLVNRSVIAGYTAMLCCAV

RGSPKPKISWFKNGLDLGEDARFRMFSKQGVLTLEIRKPCPFDGGIYVCRATNLQGEA
                    RCECRLEVRVPQ"

Figure 10 continued (SEQ ID NO: 42)
ORIGIN
```
    1 acctcactaa aggacaaarc tggagctcaa gtgatctgcc cgcctcagcc tcccaaagtg
   61 ctgggattac aggtgtgagc cacttcgccc agcccatttt tatttttta ttattattct
  121 ttgagatatt aataataaaa aataataata aataatattt ttattattat tatcactctg
  181 tcacccaggc tgcagtgcag tggtgcgatt ttggctcact gcagcccgga actccctgga
  241 ctcaagcgat cctcccacct cagcctcctg ggtagctgat actacaggtc cacaccacca
  301 cacctggcta atttgtgtgt gtgtgtgtat ttattttatt ttttattttt ttagtagaga
  361 tggggttttg ccatgttgcc caggctggtc tcaaactcct ggcctcaaat aatctgcctg
  421 cctcggcctc ccaaagtgct gggattacag atgagccacc acacccggcc taacattttt
  481 aaaattataa acccacttca tacgtgtgac aatcctgtgc agtgggtgct gctttcaccc
  541 accccgcttt acagatgagg aaaccaggtg ctttgagatt aaagagatgg cagtgctagg
  601 actcagagac accctggccc cagggtctgt ggacatgacc actgcctgaa ctgcctgcga
  661 ggatgctcct gacccgttag ccttagggtt atgggcccag catgctccca ccgtacaatt
  721 tgctgtaaga gggacacaca cggggcttgg agtaccctg aggcttgcca aaggttgggg
  781 aggcagaatt gtgctgcggg gggtgagggg aagggacag gagccagcca gggacaatgt
  841 ggccctacct tctccctgga gagacctcag ctctctggaa ttcatctata tttagcaggt
  901 ggctggacag gaggcagata agcagagcct ggggaggggg gaggtcccca tatatagtgg
  961 gaaggacagg accccactca gtccctcttt ggtgacctg tgcctgcttc gtgcctggtg
 1021 tgacgtctct caggatgcct gagccgggga agaagccagg tagctttagg actggggttg
 1081 ggtctaagtg tgggagcagg ggggtgtcta caattgggga gcagggctag gagggagttc
 1141 ttgaggggt tgacgaggac gtggcctctg agccccagga caggggcagc cagtcctcca
 1201 gggtccttt ttgattctcg gtttctttt cccatccctc tgatgagagg tgaaggtaaa
 1261 cccaaggtca gggacgcaga gaggggacac agccaagaca ggaagcaccc ggggtcaacc
 1321 cattctgaga atgcaaaggg acccctcccc tgtcccattg ccttcacctt ccacagcaag
 1381 gttccccgcg gacagagccc acgtttagta tggagctgag ccaggctcac ggcatgcctt
 1441 cagaccagtc tctaccccact atgggtctca gtctcccaac ctggggtgcc ggggtggtg
 1501 gtggcattgg gttggttcct cctggctgtg acattatctg cttcatgagc ctgtacggtg
 1561 tggcccccat gttgagggtg acacagcccc tcttctctga gagaggacag tcaggagccc
 1621 ctgaacccag gccaagggca gggaaaatca gcccaggg acctgggcct gggctgtgcc
 1681 cttatgaagg ttgtccaggg cagagatcca ggtccccatc ccccagcgcc ctcccaggcc
 1741 agctttatct cagttgctga tacccagcct gaggtccttg gaggacaaat ttggccacat
 1801 tccaagtggg cagacttccc cgccccctgc caagggcccg aatggttgg gggaaaggga
 1861 gctgggttca tcacggtgt ctccaagcag ggaaagtgga cacatgcaga aaaagtcttg
 1921 ttgggaggtc aggaccacag ccctggctct cccgactgct agctgtgtga tcttggagga
 1981 gccgcttagc ttctctgagc ctcagtgtcc tcctctgaga aatgaacaga ataactgcaa
 2041 ctacctcaga gaactggtag agtattacgt gaggggatgc atagaaagtg ctagcacagt
 2101 atttactgag aggggctgca ggggcggggt gcacgctcca accaggggcc gctgtagcct
 2161 ccacctggcc cttcagtctc agcttttagc aagaagccac ggtcagtgga agtggccgca
 2221 ggcagccctg ccgtgttcga ggccgagaca gagcgggcag gagtgaaggt gcgctggcag
 2281 cgcggaggca gtgacatcag cgccagcaac aagtacggcc tggcacaga gggcacacgg
 2341 catacgctga cagtgcggga agtgggccct gccgaccagg gatcttacgc agtcattgct
 2401 ggctcctcca aggtcaagtt cgacctcaag gtcatagagg caggtaagat cctgatcagc
 2461 cttcctgag gtttgggctg ctgggggagg ggcagcccag cgactctcca tccatccagg
 2521 gaacaggagg tgctttcaca ctttcttgcc tttgctgtgg ctgtgccccc cgccaggaac
 2581 gcccttccc ccttttctgc acatgacctc tctgagtacc cccatgtgcc atcctggctt
 2641 gttccagcca tggggtaggt gggagagatg aacaagacac aaccccactc tcccctgca
 2701 gacctccctg gggagatgac cctgcacaga cggccgggaa gccccaggag ctgtggatga
 2761 ggggagtgca gcccagtctg aggggctgct ctaaggctgg gcagagcag gatggaccct
 2821 ggagctgttc agggcagatg cagaggacat gggaactgat ggcctgggac ggggaggaga
 2881 atgtgagagg caggctggct ctccagctca gcatgagctg cctctgaggg gcccaggcag
 2941 cgggaggaca gccatggcag actttcctca tccacagcgg gctcatgggt ccaatgctca
 3001 ggagagagag ggtggagggg tctctggtta gtggctgcac cacgactccc atctgatccc
 3061 ctccagagaa ggcagagccc atgctggccc ctgccctgc cctgctgag gccactggag
 3121 cccctggaga agccccggcc ccagccgctg agctgggaga aagtgccccca agtcccaaag
```

Figure 10 continued

```
3181 gtgagagggg ctgggcaggg aggggcagga tccgtgggta gggcgtgtcc agggcaggtc
3241 tcaaaagcct ttgctgggcc aggtgcggtg gctcaggcct ataatcccca gtactttggg
3301 aggccgaggt gggcggatca tgaggtcagg agattgagac catcctggct aacatgatga
3361 aaccccatct ctactaaaaa tacaaaaaat tagccgggcg tggtggcggg cacctgcggt
3421 cccagctaac ttgggaggct gaggcaggag aatggtgtga acctgggagg cggagcttgc
3481 agtgagccga gattgtgcct ctgcactcca gcctgggtga cagagcaaga ctccatctca
3541 aacaaacaga aaaagccttt gctcacaggg tcaagctcag cagctctcaa tggtcctacc
3601 cctggagccc ccgatgaccc cattggcctc ttcgtgatgc ggccacagga tggcgaggtg
3661 accgtggtg agtgtgagct gctgtgccca gcattggggt gggaagggg ggcagcagga
3721 cactccccaa gccgggcctg tcgccctgcc tttgcaggtg gcagcatcac cttctcagcc
3781 cgcgtggccg gcgccagcct cctgaagccg cctgtggtca agtggttcaa gggcaaatgg
3841 gtggacctga gcagcaaggt gggccagcac ctgcagctgc acgacagcta cgaccgcgcc
3901 agcaaggtgg gtccaccggg gtcgtggaga cacggagaga ggggacatgg agagccctag
3961 aaggcacaag gcacacagag ggcaccatga gacccagagg cacacacgag ctgcaagcaa
4021 ggggtgtggg gaatctggga ggcaggtgga ggggccaggg gcccacaggg agatcccgga
4081 ggcctggggg ccaggagtg cgatgaggct catgggagca ctgtcgggga cctgggagac
4141 ttggtggaca tgatcacctc aaggggcac ctaataaggt ttggccgggg gtgggggggc
4201 gcccagggtg gtcaggaagc ctggaggaca ctgtgaagca tgggggcacc agctagtggg
4261 gttgtaaagc cccgggatgg gtgagtatca gggctaaggg ctcaagggac tctcagggat
4321 taaccagaac aattcctcat tatacagaca cggaaaccaa agcttgagag gttaagtggc
4381 tgctccaagg tcacttagac ataggcctag aaccttaagc cttcgttttt tgtgttttgt
4441 ttttttccgc cctgcccacc agaaccttaa ggcttaagtc cccttgtttg ttcactccaa
4501 gcctctgctt ttcccaacct tccccagtcc tgggctaggc aaggggcct ctagcaagag
4561 aggccaacat gttctgctgt gcgggctgt gcattgcaca aaagcctgta tttcaccaca
4621 accgtgtgcc agcagatggc aatcatgggt ttcgagatag tccccttctt ctgtacaaaa
4681 actctgtatg ggttaactaa agcctgaggg tgcgaagatc gatgagcatt tgtcactccc
4741 agcctccttt aaatatatat atatatatat aatttgagac agggtctcgc tctgtcgctc
4801 aggctggagt gcagtggctc aatctcggct cactgcaacc tccacctcct gggttcaagc
4861 gattctccca cctcagcctc ccgagtagct gaaactagag gtgtgcacca ccatacttgg
4921 ctaattttcg ttattttag tagagacgga atttcaccac gttggccagg ctggtctgga
4981 gctcctggtc ttatgtgatc cgcccgcctc agcctcccaa agtgggatt acaggcctga
5041 gccaccgcgc ccggccactc ccagtctcct ttaagggtgc ggagccttgt ctcccggccc
5101 ctggtgtccc ctgacgcccc gtccctccat gcacacaggt ctatctgttc gagctgcaca
5161 tcaccgatgc ccagcctgcc ttcactggca gctaccgctg tgaggtgtcc accaaggaca
5221 aatttgactg ctccaacttc aatctcactg tccacggtga gggggccctg tgtctgtcc
5281 tgggctcggg ctccccatgg gtcctggtct cctacctcct tttcccaaca ctaaggagga
5341 tgcctcgtcc catccagaca tgagtgctgg ccacgtgccc agtgctgcac acacagggtg
5401 tgagagaaac cccaaggctt gcagggtagg cgtgggggct tagggctgag tccgggtctc
5461 atctgggtgg gactctgttt tatcatcttg gtgtcacggc tcctggccca cggcctggca
5521 ctgtctgaat gtttgggcga tgggtgaagg tgagttgaga gatggtggg aattggggac
5581 aataaaccgt cccacctgcc tggtaccttg accctgggaa aggctgggaa ggtgagatcc
5641 tggggcagat gcccagcctc atgggtcat gaatgggcaa gtctgtgaat actcagaggc
5701 cgcccccagg gcaggcttc tcaaacggcc ccctctgaag ccccttcccc catctctcca
5761 ccctttgaac ccagaggcca tgggcaccgg agacctggac ctcctatcag ccttccgccg
5821 cacgtgagtg gccatcctca gggcctgggg gaggccagtg ctggagtctg aggcccttca
5881 gggtctcgac tgggggtcag ggctgggat gatttgcggg gcggagctga agtcagtggg
5941 ggctgcaggg gagagcaagc ttcccaggca ggtgaggata ctgagtctaa ccccacagg
6001 agcctggctg gaggtggtcg gcggatcagg taccctgcc caggcccta cctgcaccat
6061 ccgcagaccc caggggtct gagacgggtg ggagcccaat ctggctagtg tcccttctc
6121 cctccccact ccactcccat cctgctccta atcccttcc agtccctcac tgcagcctca
6181 ctggggtcc ctctccatag tgatagccat gaggacactg ggattctgga cttcagctca
6241 ctgctgaaaa agaggtgagt cctgggtggc agttcctggg gcagctggtg aggcctggct
6301 ccaaatccca gcactgtggt ttgccagctg tgtgaccctg agcacaacac tgcacctctc
6361 tgagttggtt tccttgtctg tcgagggat gatcccagtg tggaaggagt taaagggctc
6421 tgcagacatt atgtcccgtc aacagtcatc ctcacagtgt cccccacggc cactccacac
```

Figure 10 continued

```
6481 ttgaggctgc aaaagctccc tccgtaaact ccggggaccc agaaggaaca gagagagggt
6541 ccccagagct gcagggtcta ccaggtcggc ccaactgact tatgttctct ctgccctctc
6601 tctccctctc ccccggcccc tccattatgg ctgctgctgc tgtggcccag agagtaagaa
6661 tcggggtctg ggtgtttggg ggcggcaggg cgctggtggg tgcagagggg attcccgtcc
6721 cctctctgag aggctgtggt gagagactca gagcagggtg cggctcccca cggacagggg
6781 tgagtctctg tgccttgggc ttctcctgcc acccacctat ctgtcagagc ttaggaggga
6841 taagaaaaag taatgcacac aggaggtcct gccagagcct ccggagcagc atgggtgccc
6901 cacaacacag ggagtgcaag tgcggaaaat agggaggaag taaaggccca tgggtggggt
6961 ccaggtcttt gagggaaggt ggccataccc tctcatgtgcc acctacccft tctcccaccc
7021 ccaccccfgg agcagcagtt tccggacccc gaggtgagtg cccaacatag cacagcaccc
7081 tcatcacccc taattctgcc aggagcccct ccagatcccc agccctctt cagctcccff
7141 ggcccccagt cctgcctggc ctgggaccca gagcagctcc agctgcccca ccagaaggga
7201 aggggcagag ggacagggft ggctacagct ccttggtcct gggcccagga agccccgccc
7261 aggggctgc agtcttgccc ccggccacag cctagactgc gggacacagg gactcgaagc
7321 tggaggcacc agcagaggag gacgtgtggg agatcctacg gcaggcaccc ccatctgagt
7381 acgagcgcat cgccttccag tacgcgtca ctgacctgcg cggcatgcta aagaggctca
7441 agggcatgag gcgcgatgag aagaagagca caggttagcc cttcctcaga ggggagagga
7501 gagggcacag gctagcccft cccfacacag gagaggagag gcataggft agcccttccc
7561 cacagggaga ggagagggca caggttagcc ccccaccfcg tccacataca tggaaagagc
7621 ggagtccggc ttagcacaga gactcacagg aaagaagagc ccaggttaac ccctccttgt
7681 gtagaaaaag ccaagaatgc ccaggttagc cccttaccac agagatagaa gagaagagca
7741 aaagftaggc caggacagcc acaaggaaaa ggacagagct caggttaacc ctcctcacca
7801 aggaaaatc aggctacact ttctttctct accctcttct gaaaagaaat gaagcccggt
7861 taaccctctc cacacccaaa agaaaaggga agaggcccgc taagcctgga gagccacaca
7921 caggcaaaga aaagagcctg gctaatctft ctctcaggca aacaaagcag gagggcttgg
7981 gttaactacc ctcaccccca ggcagatgga aagaggagag cccaggaata gcccttctcc
8041 actgaggggt tgacaagggc gggtgtgagc cgggaaagca gggfctcac atgccttctc
8101 cccaccatgt ctgggtctag cacagggcct ggcacacacc tcgagcgctc tataaacacc
8161 gactgaatgg aggggtcagc ttccatgcag gatatgggag acaagcccct cccaaagcac
8221 acacacaaaa cacacacgat catggggacg gggagaggag ctggftagtc cctccctgct
8281 gacctccccc aggcccctta tccctctgcc ctgcctccct gttgtctcag cctcactggg
8341 tttcccatca ccccatcgct aggtggcctg gcccftaccg gcaccgtggc cccatttaag
8401 ccagggatcc cctgaatgcc accaatgttc ctctggfta actcctgaac tgctgagccc
8461 agagggcacc aagcaaagga ctgtaggtgc ccaaggagga aaagatggag gctggcaagg
8521 cagatgggga cctccgaggg tagggtgtc ttccaggaat agcaacaaca gtaaaaagag
8581 caaattgctg gccaggtgca gtggctcacg cctgtaatcc cagcactftg ggaggccgag
8641 gcaggtggat cacctgaggt taggcgftca agaccagcct gaccaacatg gtgaaacccc
8701 gtctctacta aaaatacaaa attacctggg catggtggca ggcgcctgta atcccagcta
8761 ctccggaggc tgaggcagga gaatcacttg aacccgggag gcagaggftg cagtgagtca
8821 ggattgtgcc attgcactcc aacctgggtg acagaatgag actccatctc aaaaaaagtg
8881 agtgagtwgc cttcctaagc cagccactag gtgctttatg taattatctc atttaattct
8941 cgaaacaaca ctatgaggag aggactatta ccatttccat gttactgagg aaaccgaggc
9001 acagagggft taaggaacta gcgcaaggtc acagagcacc cagcagtgaa tctctgcccc
9061 tccgcagctg actccaggcc cagccagagt atttgaggac tcaggggtcc ttctctgctc
9121 ggtggatgga gcccccactt cctccctggg ctcagcagca gcaacatggg cttttacaaa
9181 cacggccgca agaggaggca ttgttgtgga gcagggctgg gctcaagacc cagctctgcc
9241 acacacctgc tgggctggtg gcattgggcc agtcgcctct ctgagcccta ttccccactg
9301 cagcagcatg gggacacgca ctggcctggg ggctgagatg gagtgagwgw gactskgcac
9361 agaggctgct agtggagcgc ctggcagagt acacactcag ggttgytgag agagagaggc
9421 acagctgtcc agcccagtct ctgacagcts ygtcttctgg agccctaacc catccttgag
9481 tgagcagtga gagacoccaa ggagacagag gacaagntct gacagacaga gaccaggagg
9541 tgggttgaca cctgacacga taaagaaatg aagacaccat gcctgtaatc ccagcacftt
9601 gggaggctga ggcgggcgca tcacctgagg tcaggattfc aagaccagcc cggccaacat
9661 ggtaaacccc cgtctctact aaaaatacaa aaattagctg ggcgtggtgg cacatgcctg
9721 taatcccagc tactcgggag gccgaggcag gagaatcact tgaacctggg aggcagaggt
```

Figure 10 continued

```
 9781 tgcagtgagc caagatggcg ccattgcact ccagcctggc aacagagca agactctgtc
 9841 caaaaaacaa acaaacagac aaacaaacaa aacaaaaaga aatagagaca cagagaagtg
 9901 gaagcggggc ggcacagagg ggattggagg gggggacctg ggccccagcc acagccacag
 9961 tagcttggcc tggggagca gggtgcggc ggtggggtgg tcggggctga ggggtggtgc
10021 tcagcctttc agaagaagct ggagccggcc taccaggtga gcaaaggcca caagatccgg
10081 ctgaccgtgg aactggctga ccatgacgct gaggtcaaat ggctcaagaa tggccaggag
10141 atccagatga gcggcaggtg cagcctgggg tggggagggg ggctcgggtg gaggtgggga
10201 cccccatagc cttgcctcct gccctctcc acatgcgtat ctctgactcg gtgtggctct
10261 cagccccatc tctctgggcc taatttccca tccttttgct cctgccggtc cctctctctc
10321 tctccttttg tctcgggctc acttcctccc gtcgggaaca cttcaacggc cccttctgtt
10381 ctacagcaag taagttcccc tctggatggc ttggggtggg gggcacaggg attatcacgg
10441 ggcgcactgg gcccggaggg gtgtccgcag ctttcctgcc acttccctgc ggcccccacc
10501 caggtacatc tttgagtcca tcggtgccaa gcgtaccctg accatcagcc agtgctcatt
10561 ggcggacgac gcagcctacc agtgcgtggt gggtggcgag aagtgtagca cggagctctt
10621 tgtgaaaggt gggcctggga cctgaggatg tgggaacctg ggaggagat ggcctcaggg
10681 gagccaaccc tcatgctcac cctgcctgga cagagccccc tgtgctcatc acgcgcccct
10741 tggaggacca gctggtgatg gtggggcagc gggtggagtt tgagtgtgaa gtatcggagg
10801 aggggcgcca agtcaaatgg tgagttccag aagcacgggg catggtgtt ggggcatct
10861 gcccagaaga ggccacagca cttgccaccc acccacccgg ctaggctgaa ggacggggtg
10921 gagctgaccc gggaggagac cttcaaatac cggttcaaga aggacgggca gagacaccac
10981 ctgatcatca acgaggccat gctggaggac gcggggcact atgcactgtg cactagcggg
11041 ggccaggcgc tggctgagct cattgtgcag ggtgagcctg gctgggggg cacatgaggc
11101 tttagggctt ggaccctca gcccccaccc cacctagccc tgtaggggag caggcaaacc
11161 tgggctcaag gcctctgtga ccttgggcct ttgacagcct aaacctcatc cttctcatct
11221 ctaaaatgac gatgctgagg tgaccgctcc agagggtact gagagggtca tacgggcctg
11281 gtgagcatca ccaccccctca gacacttgag gttccttatg tgcactgcac catcacaggc
11341 aaacatggca cacacaggca cacgtgtttt cacatgccca catgcaccca gacacgtgcg
11401 caccagcgcc catgggccca cacgccctcc acaggattc acgccacacc cacacaccct
11461 cccgagctca atggctctgc cctgccctgc agaaaagaag ctggaggtgt accagagcat
11521 cgcagacctg atggtgggcg caaaggacca ggcggtgttc aaatgtgagg tctcagatga
11581 gaatgttcgg ggtgtgtggc tgaagaatgg gaaggagctg gtgcccgaca gccgcataaa
11641 ggtgtcccac atcggcggt gagtgtgcag ggcaggtgga tgggacaggt ggagactgag
11701 atggagacag agagagacac agggagaaac agagagagag agataaagac aggtggacag
11761 agaggcagat gcacagagac aggacagaga ctgagacaga gacccacaga gagggagaaa
11821 cagacagacc caaaaagaca aagagacaga aagacagaaa tagttctata gagacagaaa
11881 gatatgcaca ggggaggcac acacatagga gagttcgtca gagacagaga agaacagagg
11941 gacagagaca aagaggcagc agggagagac acggacgggg tcgagagctc cccagcaccc
12001 tcccccagct tgtgaccagg gcagggcagg aggccaccaa ggaggccggc tctggccaga
12061 ggccctcact gcctctcccg ccctcttgct catccctgga gcaactgggc tggccgtgct
12121 gggcccaagt tcacagagat taatgagacc cagcccctgc ccagtctcca agggcccagc
12181 caaggagatg ctttgatgta gaaatcactt ttacgctgcc tacctctgaa ggcacattaa
12241 aaagctggaa aattagataa tatagaaaaa aaaaggcatt tttaaaatc agaataccaa
12301 caagccagga caaggtgagg gcctcctggg accctggctg gggtatctgg caaggccagg
12361 ggtgtgtggc ccagtggggt cccctgagcc actgctcccc tgcagggtcc acaaactgac
12421 cattgacgac gtcacacctg ccgacgaggc tgactacagc tttgtgcccg agggcttcgc
12481 ctgcaacctg tcagccaagc tccacttcat gggtgagcct gctccagggt agggtgggtc
12541 ggggcagtgg ggccaggagc cctgtcact gggccctgcc tttgcccccg tgctacttgc
12601 tcttccttct cttcagagg tcaagattga cttcgtaccc aggcagggta agtcttgggg
12661 cccctgagtc ttggttctgc tcactttccc gcaacccacc cacgcaggcc tcccctccac
12721 tcacagaggg aagagcaagg atcaaaagtg ggggtcctgg ggccagctc cagctttgcc
12781 actcatgacc atgggtcaat tataatctct gtgagcctca gtttcctctt ctctaaaatg
12841 ggaaccctga tagtgccacc tcataggata gttataaaga tgaggtgaca tgatgtatca
12901 gacctgtcaa gtgctgtcac acgtgtgact gttattatta catctttct tcttcttcct
12961 ttttttttat ttttatttt tttgagacgg agtctccctc tgtcgcccac gctggagaga
13021 gtggcgcga tctcggctca ctgcaagctc cgcctccag gttcacacca ctctcctgcc
```

Figure 10 continued

```
13081 tcagcctcct gagtagctgg gactacaggc gcccgccacc atgcccagct aattattttt
13141 tgtattttta gtagagacgg ggtttcacca tgttagccag gatggtttcg atctcctgat
13201 ctcatgatct gcctgcctcg gcctcccaaa gtgctgggat tacaggcgtg agccactgcg
13261 tccagactgc tttgctttgt ttaactgagg gcagattcct gatttatttg gccagggaac
13321 cttttaatg tgtgcatgtg tgcgtgcatg tgtgcgcgcg tgcgtgtgtg tgcatgtgtc
13381 tgtgtgtgta tgtatatatg tgtgtctgtg tctgtgtgtg tgcgtgtatg tatgtgtatt
13441 tgtgtctgtg tgcatgtgtg tgtctgtgtg tgcatgtgtg tatgtgtatg tgtgtctgtg
13501 tgtatgtgta tatgcgtgtg tgtgtgtgta ttgtgtgtgt gtgtatgtgt gtggcaagac
13561 actgatgttc ccccagtttt caaaatgcta tgctaggtga cctgacctga atattacaag
13621 cctcccagcc aacgtcctgg ggtgatggga atgttccaga tcttggttgg attaataatt
13681 gcatgggtgt attcatctgt cagaactcag cctactgtca gatctgagca taaactatac
13741 ctcaatacaa atctaaaaaa ccaataacca ggggcccagg ctcttgagca gccccgcccc
13801 agtgacctgt gctcctcctg gctctcccgt ttctctgaac tacattgtgt cttctgcaga
13861 acctcccaag atccacctgg actgcccagg ccgcatacca gacaccattg tggttgtagc
13921 tggaaataag ctacgtctgg acgtccctat ctctggggac cctgctccca ctgtgatctg
13981 gcagaaggct atcacgcagg tactgtgggt ccctcctcag tctccccatc tataagatgg
14041 gtgtgtggaa ccagccaagt gctaggacct gctgcacacc ccacccacat gtgcacgccc
14101 tgctgttggc taccccgtgg gagagactgg tcaggggca ggcaaggtgg gcagtgtggg
14161 tcaggggtg gaagaagcag cagagggcg cttccaggct gagtcagctc ctctgctccc
14221 tacttccctc ctgccctgtt cccaggggaa taaggcccca gccaggccag ccccagatgc
14281 cccagaggac acaggtgaca gcgatgagtg ggtgtttgac aagaaggtga gtgagactga
14341 ggtcaggagg aggctcgttt gtctttcatc actttctacc tacgtggtgc cgagcccttg
14401 gcgaggtctc catggaggtg ccacacttgg ccgggtgtgt tgctgccccc agcagggtcc
14461 ctgtggggcc ctcacacctc aggcagaggg tctctgtgaa gtgtgctgat ggccatcaca
14521 aggatgtgga caccctctca ttgccaggaa gccctcatga ctgggctgct ccctggctcc
14581 cttcatccta agctgacctt gaccttgacc ttgtgctccc tctcaactca ggagtagttt
14641 ctgagacact tttctgccag tgtagctgcc ggggtcttgc tcctgcctgg cactgttggt
14701 tcttctgaag gctggggtct tgaggggtcc tcatgatagc tcatctgaga ggacaggtgg
14761 ttgccccagg tcccgtgaca aagctagaac ccgagcccct gccctcagtc ggtgccacag
14821 agatgatttt gaactagatg ctgacgtgga tgcagtcttc ccacaggctg tgttccccc
14881 atggaccccc gggacatctg gctgttggcg gaggctgcaa gggcctctgg ggtctgactt
14941 ggatctcacc ccaactctgc accccccag ctgctgtgtg agaccgaggg ccgggtccgc
15001 gtggagacca ccaaggaccg cagcatcttc acggtcgagg gggcagagaa ggaagatgag
15061 ggcgtctaca cggtcacagt gaagaaccct gtgggcgagg accaggtcaa cctcacagtc
15121 aaggtcatcg gtgaggccgg ccggggtcca agctggagaa cacagagggg cagccccaag
15181 gagggcccat ccgttcgctc attcagccac tcgacaaaca tcacgggcat gctccctgag
15241 ccgagcggca acaggacagg ttttctgcc caaaaggagc cccgctctgg ggagatgga
15301 ggcagatgca tccagcagat ttcctgcgac actgctgtac atgagccatg tccagagtgc
15361 cgtgggagca ctgagcagag agccatccct gtgcctgggg gtgatgcctt taggaggctg
15421 agaagatggt gaggaaagc atcccaggca gaggaaactg tgtacaaagg ggtggaggag
15481 ggaaagggcc ttttgggtgt ggagaatgaa tgaaacatgt caggagagga ctgggtgggg
15541 ttgggaggat cagagccagg acagggtga atatgggcag tgagaagcct taaagggttg
15601 acggagggct ggcgacatga tcagaaatgc atcctgttga gacccagcct ggacaacaca
15661 gtgagactcc atatcactaa aaaaaaaaa aaaaaagga aagaagaaa gaaatgcatt
15721 ctagaaagat ctctttggat ctgggggtgg tggggcagc ctgtggcggt tagttggagt
15781 gggaagggga cgagcaacgt tactcaaggc ctgagcgggg cagggctgat gtgggtccat
15841 cccacccccat ccagacgtgc cagacgcacc tgcggccccc aagatcagca acgtgggaga
15901 ggactcctgc acagtacagt gggagccgcc tgcctacgat ggcgggcagc ccatcctggg
15961 tgagtgcaag ggcaccggat ggaggtgtga gggcgccaaa cagatccgag ggaaggtggt
16021 gtgggatgc ctgggttcca gaccagagct gccacctccc ctgagccagg ctacatcctg
16081 gagcgcaaga agaagaagag ctaccggtgg atgcggctga acttcgacct gattcaggag
16141 ctgagtcatg aagcgcggcg catgatcgag ggcgtggtgt acgagatgcg cgtctacgcg
16201 gtcaacgcca tcggcatgtc caggcccagc cctgcctccc agcccttcat gcctatcggt
16261 gagcctgcct ggcctggtcc tgcccccgc cccctcccca gttaaaaacc tccaataata
16321 gcaggtgctc tgcaggcagc catgctagac actcacatcc acagtctcct ttcatcctcg
```

Figure 10 continued

```
16381 actggggata ctcagccgca ttttacagat gaggaaacag gctccaagca gttaaatgac
16441 ctgcttgaga tctcccagct ggttggggtg gagctgactc tcacactacg ccgacccta
16501 gttcacgttt caagcctctc tttccatgtc tacaaaatgg gaataatgac actgcctatc
16561 tcagagagct gttaggatga tatgggatga ccaggcaggc catctggcat ctaacaggtg
16621 ctcaataaat gttcattgtc ccctgttctc cacacccttc aacccaggg tttcacctat
16681 gggatggggc aagggctgta gttagtggag gggtctcagg ggcatctgtc tgtggaaaga
16741 gtcctggacc aagactcaga gatggcagag gcagctccat ggtccccggg gggccaactg
16801 gagtcatccc tccctgaagc ctcagcttcc tcatctgtat aatgggtct gagtgggcag
16861 aacaggtgtt gagactgtgg cagggctcag gaggacacct gttcccacta gggtgggtga
16921 gtccgggggc agctgcctgt ggcaagggca ggccaaggac ccctgggccc agggatgggg
16981 cacagcttgg gaagatggca ggaatcgggg cctgtgggga gaagggtcca ggcctctcgt
17041 tttagggact gattcctggt ttgttcagtt cttagtcaac tcacctaatc atacgtgcca
17101 ggaaattccc atgttttctg tagttttagt tttagttttt tttttttttt tttttttg
17161 agatggagtc tcgctctgtc acccagactg gagtgcagtc ctggcgcgat ctggggtcac
17221 tgtaaccttc acctcccagg ttcaagcaat tctcccacct cagccttctg agtagctggg
17281 attacaggca tccaccacca tgcccagcta attttgtat ttttgtagag acggagtttc
17341 accatgttgg ccaggctggt cttgaactcc tgacctcagg tgatcctccc acctcggcct
17401 cccaaagtgc tgggattaca ggcgtgagcc accgtgcctg gctgctgttg ctgtttgttt
17461 ttaagccaat ctacagacat gtcttgtaac agggacaaaa tattccttaa agtggccaaa
17521 agccagctga acaggaagtg cccctatgt gaccagtggg cagttcagag tctagggcat
17581 ggatctccag cttccccagg cttgctcaga cccctctctg acctctcctc tgcccaggtc
17641 cccccagcga acccacccac ctggcagtag aggacgtctc tgacaccacg gtctccctca
17701 agtggcggcc cccagagcgc gtgggagcag gaggcctgga tggctacagc gtggagtact
17761 gcccagaggg ctgtgagtgt cccgcccc aaccccctc cccaaaggaa gaacatgctc
17821 accttgccat tgagcagatt cacctgtagt caagtttttt aggcccactt ttgccgaaag
17881 ttgaggacac ccagagaaat atctgtcctg ttttcagaag taaaaaagct tgcctagtga
17941 aaaacaaatg cagagtaaag ctgactgtaa cacttctttg agcagtgcga aatcagcaac
18001 tacattttaa aaacatattt aaggccaggt gcgatggctt acgcctgtaa tcccagcact
18061 ttgggaggcc aaggtgggcg gatcacctga ggtcgggagt cgagaccag tctgaccaac
18121 gtggagaaac cccgtctcta ctaaaaatac aaaattagcc gggtgtggtg gtgggcacct
18181 gtgatcccag ctacgcggga ggctgaggca ggagaatcac ttgaactcgg gaggcagaag
18241 ttgcggtgag ccaagatcat gccattgcac tccagcctgg gagacaagag cgaaactcca
18301 tctcaaaaat aaataaacaa ataaaattt aaaaaaacat atttaaatcc tggagattcc
18361 tatcagagga gtgggcagtg ggagtggggt gtcagtggtg acacagcctg tggccttgcc
18421 tccccctccc cacccccagg ctcagagtgg gtggctgccc tgcagggct gacagagcac
18481 acatcgatac tggtgaagga cctgcccacg ggggcccggc tgcttttccg agtgcgggca
18541 cacaatatgg cagggcctgg agcccctgtt accaccacgg agccggtgac agtgcaggag
18601 atcctgcgtg agtgccctt tgtgcagtca caagacccgc cattgacacc ccaggccctt
18661 ggtgtccagt ggaggtgggg acagttgggg aggcccagaa tgctctgccc agaacgctgg
18721 gcagagacag gagggtggg agccatcgtc catgcgctag gcctagggaa aaagtgcaga
18781 gagggtggcc aggcacagtg gctcaagcct gtaatcccag cactttagga ggccaaggca
18841 ggcagatcac ttgaggtcag gagtttgaga ccagcctggc caacatagtg aaaccctgtc
18901 tctactaaaa atacaaaaac tagccaggtg tggtggcgcg tgcctgtagt ccctcaacta
18961 cttgggaggc tgaggcagaa gaatcgcttg acccgggag gtggcagttg caatgagctg
19021 agatcacact attgcactcc agtctgggtg acagagtgag acaacgtctc aaaaaaaaaa
19081 aagtgcagaa agggctctct tggtgtatgt cagtccctta gttctggaac agggaaagta
19141 aaagccacag tacccaagct ctcttccagg agtgtctcag ctccaacagg taaatattgt
19201 ctatgtagtc agattggtcc ctctgggatc cacttcccat tcctttgttc cttgtcccaa
19261 caaagggtcc atcttttgta aggattggtt ctcaaagctg gaacgaggca gcaaactcag
19321 gtggtaacaa cacagggcat agggtgtcaa agcccaggct tacaccctgg tctatgactt
19381 actagctgtg tgacttcagt caagttgctt accctctctg atccctgcct tttgaagtgg
19441 tgaggctcgg ggaagccagc tgggcttggg cagcctggag ttgctgtgtt agcaggagct
19501 aaaggaggcg cagggcccag caggcagctt ttttcttagc tgcagctctc tgggcctttgt
19561 ctcaagggag gttggagctg tggagcccct cagagctgtg gcgggccctc acttagctac
19621 ccactctata cccacagaac ggccacggct tcagctgccc aggcacctgc gccagaccat
```

Figure 10 continued

```
19681 tcagaagaag gtcggggagc ctgtgaacct tctcatccct ttccaggtgg gactggcccc
19741 cttccctgtc ccccagggga gagaggctat agtgtgttgt tcccatccag tggactgatg
19801 tctcagggct ggcctgatct gaggtaccag aggctgggt ggcggccggc ccttggagtg
19861 atccaggttc agggttaagc ttttcctccc ctcagggcaa gccccggcct caggtgacct
19921 ggaccaaaga ggggcagccc ctggcaggcg aggaggtgag catccgcaac agcccacag
19981 acaccatcct gttcatccgg ccgctcgcc gcgtgcattc aggcacttac caggtgacgg
20041 tgcgcattga aacatggag gacaaggcca cgctggtgct gcaggttgtt ggtgcgtggc
20101 caaggcctcc ttgagccccc ttgtttccct tccctgggct gggctgctgg ggccaagggt
20161 ggggccaggg gacccaaccc acagctcaca ttttccagtc cactgcccca gcaggcctgg
20221 ccctggttgg caggggtggg gtggtccctg gagccagtga ccccctgctc actgtcagga
20281 ggcgtggtga cccaactggg tctgtctccc gcagacaagc caagtcctcc ccaggatctc
20341 cgggtgactg acgcctgggg tcttaatgtg gctctggagt ggaagccacc ccaggatgtc
20401 ggcaacacgg agctctgggg gtacacagtg cagaaagccg acaagaagac catggtgagc
20461 ccagggtctg gggtcccac gtgcaccctg cctaggcccg gcagacccag gccgcagcta
20521 cccttcactg tcctcaccgt ggacccctca ccctccctct gctgatctga atccctccat
20581 agtaggggtg gagatgccaa gggcacccag gagaggctct cggcatcagg aagggcctgg
20641 cccagagatg cctcccctcc ctccctgccc ccaggagtgg ttcaccgtct tggagcatta
20701 ccgccgcacc cactgcgtgg tgccagagct catcattggc aatggctact acttccgcgt
20761 cttcagccag aatatggttg gctttagtga cagagcggcc accaccaagg agcccgtctt
20821 tatccccaga ccaggtgctg tacctcatt cttccaacca ggggctgggg cagggaggct
20881 gtgggaacag ggagaggggc ctagctttgt gtggcctctc ggtaccaagt cctgtcacca
20941 acaggcatca cctatgagcc acccaactat aaggccctgg acttctccga ggccccaagc
21001 ttcacccagc ccctggtgaa ccgctcggtc atcgcgggct acactgctat gctctgctgt
21061 gctgtccggg gtagcccaa ggtagggaac tttaggcgct ggtccaggcc gaccaggagg
21121 cagggctcac aggccccgac gttgagcagt cctctcccca gcctgtctcc cctgctttct
21181 ctccaccttg gggtgtatgg accgggttcc tcccctgggg cagggccatg gtactcactc
21241 ttggttccat gttgtttcc agccttgggc atagtcaggg actctcgtgg gacccccga
21301 gtagaaacac agatgtgtct ccctgggtcc ctgccaggtc ccctctcagc ctggatggct
21361 tccctccctc tctttacctt atttatagcc caagatttcc tggttcaaga atggcctgga
21421 cctgggagaa gacgcccgct tccgcatgtt cagcaagcag ggagtgttga ctctggagat
21481 tagaaagccc tgcccctttg acggggcat ctatgtctgc agggccacca acttacaggg
21541 cgaggcacgg tgtgagtgcc gcctggaggt gcgaggtgag gagccctcgg ggccagggcc
21601 tgggagatgg gaagagcggg cggcagtggg gaccctgggc tttgctccgt tgtcctcggc
21661 caagcacctg ccctggctgc aagggcacgg accctgccac gcccagatgg gcaatagctt
21721 ccagaaggct gggaggacac agtgacatgg cctcctcttc tgcagtgcct cagtgaccag
21781 gctggctcct ggggatggcc aggtatgtac caccccgacac ccagggcaca agtcagtggc
21841 tgagccctgg cccttggtcc tggggcagcc atcagtaaat gggaggctgt aggggccctc
21901 cattcactcg taagataacc tgtgttgcag gtacaaccgg atgccagccc cgtgccagga
21961 gcctggaggg aagttgggga aacccctccc tactgttgga tgtatgtgtg acaagtgtgt
22021 ctcctgtgct gcgatggggg atcagcaggg cagttgtcgg gcagtcctga gtgggtgttg
22081 cacagactgg tccacagggc tcctgaagga agcccctgga tctttggggt aaaaggaggg
22141 tggcctcaag aaacaatgtc tggggacagg cctttctggc ctgctatgtc ttcccaatgt
22201 ttattgggca ataaaagata agtgcagtca cagagaactc actcttctca atttcggtgt
22261 gcctgttttc ataaaaatgc acaggggatg gccaggtgcg gtggctcatg cctgttatcc
22321 cagcactttg ggaggcggag gcggccgat cacctgaggt caggagatca agaccagcct
22381 ggccaacatg gtgaaacccc gtctctacta aaaatacaaa aattagctgg gcaaggtggc
22441 gcgcctataa tcccagctat ttggaaggct gaggcaggag aatcacctga acccaggagg
22501 tagagtttga ggtgggccga gatcatgcca ctgcacttca gcctgggtga tggagtgaga
22561 ccatgtctca aaaaaaaaaa aagaaaaaac ccagggaca ttgatcttca agcaaagtg
22621 agagcagata ctgttttttg ttttgttttc ccgatgatta aaccaggccc agagtggttt
22681 ctgagttcat aaaacattaa cgctagaagg aacctgtctt ccctacagc attcactctt
22741 cagatgatga aactgagctg tgacagcgga aagtgcattt aactggtccc aggtgctcag
22801 cgtgatcctt gtgccagggg ccgtggtcac aaccgcctgg aggtggggtg aggcagaatc
22861 tcagtgttgt gattgtgctg gggtggagct gcactaggtg gctttggagt cccagccagc
22921 aataagccag cagcgggttc agacccatat ccccggtggg agacagcaac ccaatccagt
```

Figure 10 continued

```
22981 ccaggacgct gggcaccaga aaggtgtcag ggccagggcc ccactctgct ctcacttccc
23041 ccatggggag cctaaatccg agcatctgtt tccttttggg cgcgggaagc cagcaggtct
23101 caaattccct gagagtgcag ccaggttttt ccaggacaga attccatgaa ggcagctcct
23161 aggggagctt ctgggagttc tatgcagtgg aagacactcc tggccaggag tccggggccc
23221 tgtgggaggc cctggctgaa tcaccacacc tctctcgacc atacccacct gtaagggaac
23281 ggagagggcc agggccttgg ctttctttca cttaatctca gttcaggtga ggacgcccag
23341 tctggctgct ccctctagca gcctgttcat tcatggcagc ccagctctct gcagggccct
23401 caggtgccca ggaaggaaag ctcctcccgc agccttgctc taggagccca gaacagggga
23461 gctggggcct ccgtgtgcca aagcttggac atggatgacc tcatctcctt ccttccttcc
23521 agcctgaggt gacttttag agtccaggga tagctttcct caggcctgag ccaagaggag
23581 gtgtcattta acacaaggca gccagggagc ctgaagggag ttgaggacat ttatttcaca
23641 ttcacacaac tgtacatttt ctataaataa tgtggggctg aaatatttac agtcatttct
23701 tgcccatacc caggctgtct ctccctcctg acaccccgtg cctggagaga cagcctgcag
23761 acagatgtgc aaacccagct tggtctttcc tgcccctcc ctgatgctca ggcagagcag
23821 ccagcggtcc ctggactcc actagcctcg accactccat cctctgatgc cgaaagcgtg
23881 gcaggccaca gggaattcgc cgctccactg cagtcacaga ngctgtggca ggcagcagcc
23941 aacactgcgg gcctgggcag tactgcggct tgggaatgca naagaagcag gaggtgcact
24001 cactcggctg ccccaatctc cttcctctct gtgcctctct gagaggtgag ccaggtctca
24061 ctctca
```

DETECTING MUTATIONS IN THE FELINE CARDIAC MYOSIN BINDING PROTEIN C GENE ASSOCIATED WITH HYPERTROPHIC CARDIOMYOPATHY IN CATS

PRIORITY CLAIM

This application claims priority to U.S. Provisional Patent Application 60/686,647, filed Jun. 1, 2005, which is incorporated herein by reference, in its entirety.

BACKGROUND OF THE INVENTION

Hypertrophic cardiomyopathy (HC) is a common feline disease, and shares many of the features of human HC. Feline HC, like human HC, is characterized by moderate to severe papillary muscle and left ventricular (LV) concentric hypertrophy, as well as systolic anterior motion (SAM) of the mitral valve. HC is a common cause of heart failure, sudden death, and systemic thromboembolism in domestic cats. Because of the serious nature of the disease, there exists a need to develop reliable methods for diagnosing and preventing feline HC.

SUMMARY OF THE INVENTION

This invention is based on the discovery of genetic mutations in cardiac myosin binding protein-C (hereinafter "MYBPC"), which are associated with the development of hypertrophic cardiomyopathy in cats, particularly domesticated cats, and more particularly Maine Coon Cats.

According to some embodiments, the invention provides methods for diagnosing feline subjects, particularly domesticated cats, and more particularly Maine Coon cats, as having HC, e.g., familial or sporadic hypertrophic cardiomyopathy (hereinafter FHC or SHC). The methods provide a useful diagnostic tool for screening symptomatic and asymptomatic feline subjects. Asymptomatic feline subjects from families having a history of FHC can be selectively screened using the method of this invention, allowing for early interventional care and improved overall prognosis. Feline subjects having the mutation for FHC may be removed from the breeding population, thus aiding in the reduction of disease propagation through family lines.

In some embodiments, methods are provided for predicting the likelihood that a cat will develop hypertrophic cardiomyopathy, comprising: a) obtaining a nucleic acid sample from a feline subject to be assessed; and b) determining the nucleotide present at the nucleotide position corresponding to position 66 (codon 31) of exon 3 of native a MYBPC gene (which corresponds to position 66 in SEQ ID No: 3 and position 38 in SEQ ID No: 4), wherein the presence of a cytosine at position 66 indicates that the feline subject has a greater likelihood of being diagnosed with hypertrophic cardiomyopathy than an individual having a guanine at that position. The tested feline subject may or may not exhibit clinical symptoms of hypertrophic cardiomyopathy. In some instances, at least one blood relative of the feline subject may have been diagnosed with hypertrophic cardiomyopathy.

In some embodiments, the polynucleotide is cDNA reversed transcribed from RNA. The RNA may be obtained from nucleated blood cells. The methods are useful for detecting subjects having or at risk of developing familial or sporadic hypertrophic cardiomyopathy.

In certain embodiments, the invention provides methods for predicting the likelihood that a cat will develop hypertrophic cardiomyopathy, comprising: a) obtaining a nucleic acid sample from a feline subject to be assessed; b) screening the entire nucleotide sequence encoding the feline cardiac myosin binding protein gene; and c) detecting the presence of one or more mutations of the feline cardiac myosin binding protein gene, wherein the presence of a cytosine at position 66 (codon 31) of exon 3 of native a MYBPC gene (which corresponds to position 66 in SEQ ID No: 3 and position 38 in SEQ ID No: 4), and the presence of at least one other mutation in the polynucleotide encoding feline cardiac myosin binding protein C gene, indicates that the feline subject has a greater likelihood of developing hypertrophic cardiomyopathy than an individual having a guanine at position 66 and lacking any other mutations in the polynucleotide encoding feline cardiac myosin binding protein.

In some embodiments, the invention provides kits and methods for use thereof for diagnosing hypertrophic cardiomyopathy in cats, comprising: a first receptacle containing an aliquot of polynucleotide probe that is hybridizable to DNA that encodes a cardiac myosin binding protein; and a second receptacle containing one or more primers useful for amplifying DNA that encodes feline cardiac myosin binding protein. Such kits may also include instructions for using the components of the kit to detect the presence or absence of mutations in amplified DNA which encodes feline cardiac myosin binding protein.

BRIEF DESCRIPTION OF THE DRAWINGS

FIG. 8 shows exon 3 of the feline MYBPC gene (SEQ ID No: 3), with the mutation site containing nucleotide position 66 indicated in underline.

FIG. 9 shows the coding and non-coding regions of the feline MYBPC gene. The mutation site in exon 3 containing nucleotide position 66 is underlined.

FIG. 10 shows the nucleotide sequence for the human MYBPC gene (SEQ ID No: 42) as well as the corresponding amino sequence (SEQ ID No: 41).

DETAILED DESCRIPTION OF THE INVENTION

Figure 1:
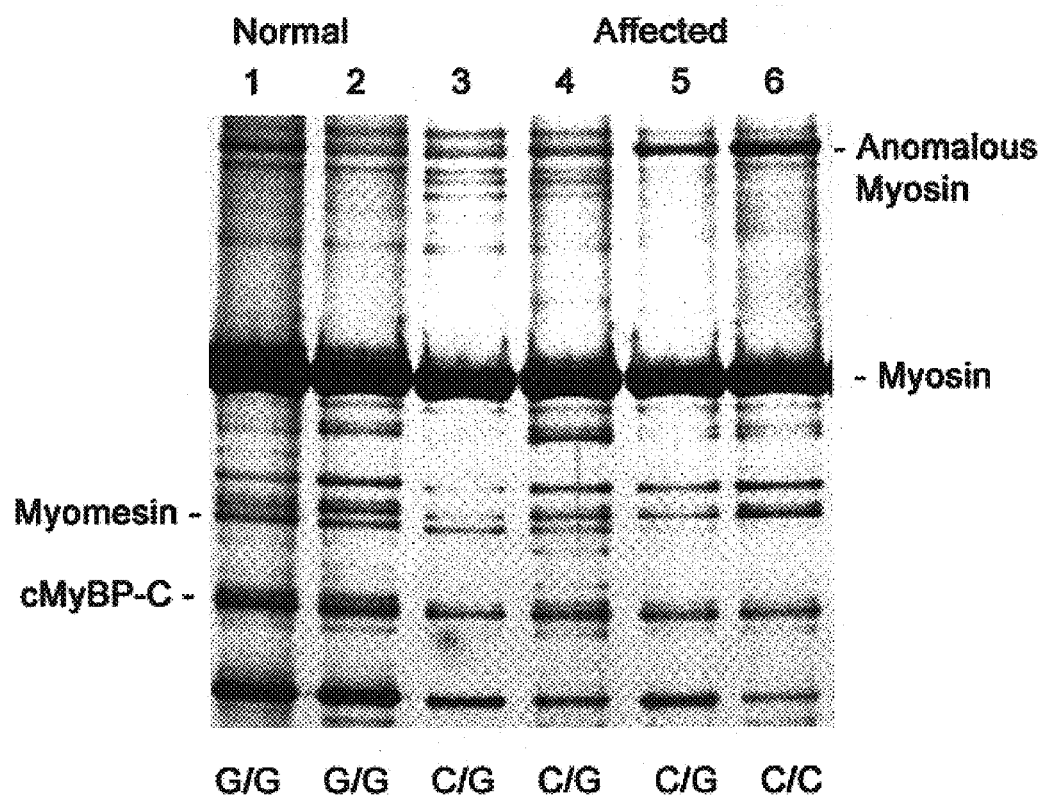
FIG. 1 shows SDS-PAGE analysis of LV (free wall) myocardial samples from normal (lanes 1 and 2) and affected (lanes 3-6) cats. The cMYBPC and myomesin proteins are reduced and the anomalously migrating beta myosin appears to be increased in comparison to the normal cats. The genotypes of the cats are shown below the lanes as G/G (normal cat), C/G (affected heterozygote) and C/C (affected homozygote).
Figure 2:
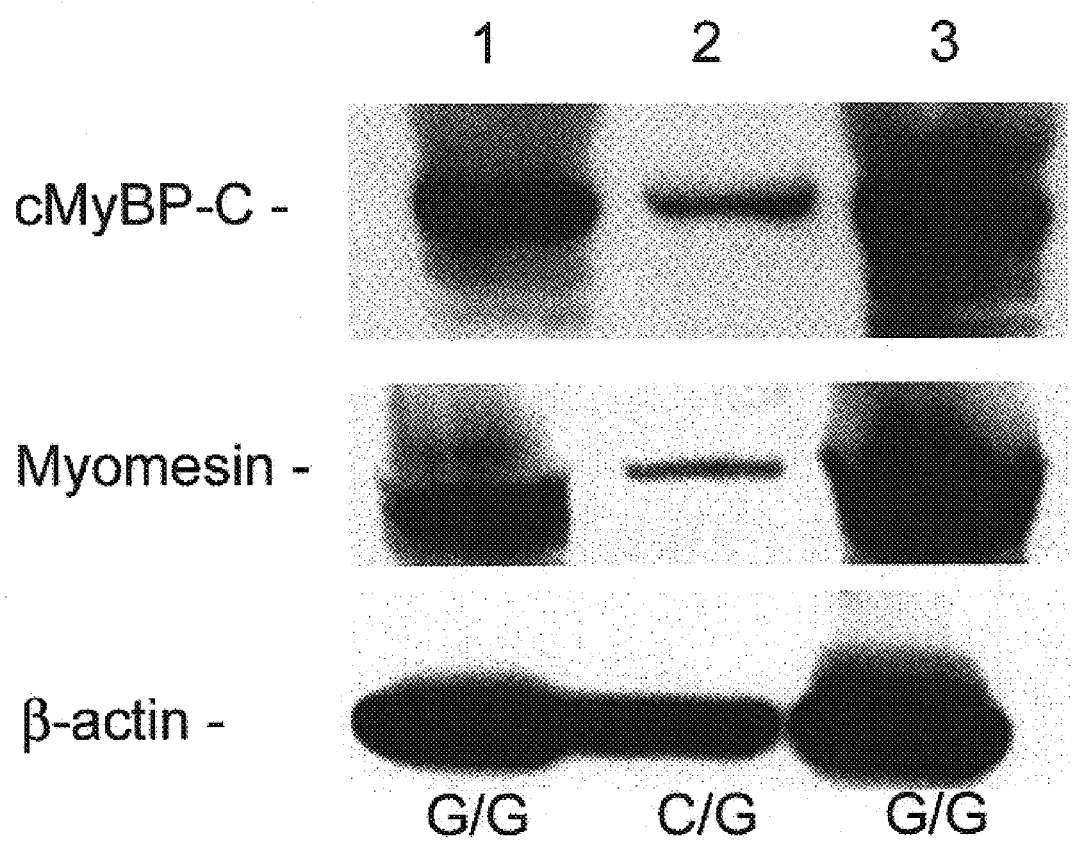
FIG. 2 shows an immunoblot performed to confirm the identification of the abnormal proteins. Lanes 1 and 3 contain myocardial samples from normal cats, lane 2 contains a myocardial sample from an affected (heterozygote) cat. The genotypes of the cats are shown below the lanes as G/G (normal cat) and C/G (affected heterozygote).
Figure 3:
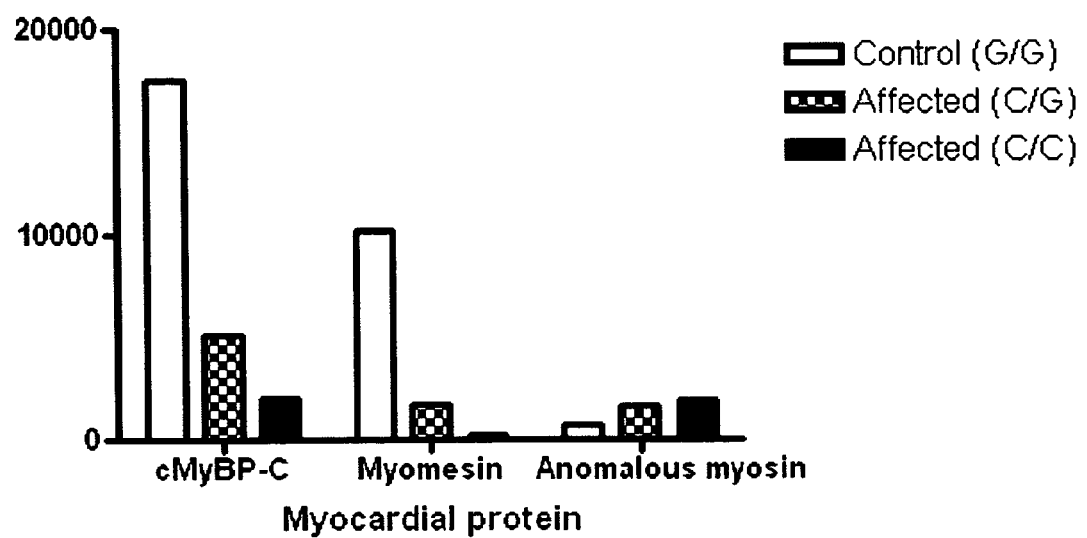
FIG. 3 shows quantitative (arbitrary densitometry units) SDS-PAGE analysis of myocardial proteins in normal and affected cats. Both the cMYBPC and myomesin proteins were significantly reduced in the affected cats in comparison to the control cats (cMYBPC, P<0.001 and myomesin, P=0.011). A weak inverse correlation (r=−0.341) was observed between the amount of anomalously migrating myosin and the cMYBPC for affected cats. The genotypes of the cats are shown as G/G (three normal cats), C/G (seven affected heterozygotes) and C/C (one affected homozygote).

The present invention will now be described with occasional reference to the specific embodiments of the invention. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurements.

The disclosure of all patents, patent applications (and any patents that issue thereon, as well as any corresponding published foreign patent applications), GenBank and other accession numbers and associated data, and publications mentioned throughout this description are hereby incorporated by reference herein. It is expressly not admitted, however, that any of the documents incorporated by reference herein teach or disclose the present invention.

The present invention may be understood more readily by reference to the following detailed description of the embodiments of the invention and the Examples included herein. However, before the present methods and compositions are disclosed and described, it is to be understood that this invention is not limited to specific methods, specific nucleic acids, specific polypeptides, specific cell types, specific host cells or specific conditions, etc., as such may, of course, vary, and the numerous modifications and variations therein will be apparent to those skilled in the art. It is also to be understood that the terminology used herein is for the purpose of describing specific embodiments only and is not intended to be limiting.

Detecting the Presence or Absence of Mutations Associated With HC in Cats

In some embodiments, the invention provides methods for detecting the presence or absence of one or more mutations associated with HC in cats. The methods are useful for detecting the presence of or the risk for developing HC in domesticated cats, and more particularly Maine Coon cats. The methods comprise providing a polynucleotide which encodes feline MYBPC and detecting the presence or absence of a mutation. The methods can further comprise amplifying the polynucleotide (e.g., using a polymerase chain reaction) to form an amplified product and detecting the presence or absence of mutations in the amplified product which are associated with HC in cats. In a particular embodiment, the methods comprise detecting the presence or absence of a mutation in exon 3 of the MYBPC gene of cats, more particularly Maine Coon cats. According to such embodiments, the presence of a single base change at nucleotide position 66 of exon 3 (codon 31) from guanine ("G") to cytosine ("C") results in a corresponding change in the MYBPC protein sequence from Alanine ("ALA") to Proline ("PRO").

For purposes hereof, the term "mutation" refers to a gross alteration in RNA or DNA or a small alteration in the RNA or DNA (e.g., a mutation in the RNA or DNA), which alters the expression, amount, sequence or functionality of the encoded protein, namely MYBPC, and is associated with the development of HC in cats. Such mutations include substitution (of a base pair), deletion (of a base pair), or addition (of a base pair at a particular target site in the coding region or non-coding region of the gene). The term mutation also specifically includes splice site mutations (e.g., 5' splice site donor mutations) or duplication mutations, and allelic variants. At least one specific mutation in a feline MYBPC gene which is associated with HC is described in the example below.

Detecting Feline Subjects at Risk of Developing Familial Hypertrophic Cardiomyopathy The present invention also pertains to methods for detecting feline subjects at risk of developing familial HC (FHC). These methods include obtaining a polynucleotide sample that encodes a MYBPC from a feline subject being tested for FHC. Feline subjects may include an individual suspected of having FHC, or blood relatives, such as the parents of such a feline subject. In some embodiments, the feline subject is tested for a G-C mutation at nucleotide position 66 (codon 31) of exon 3 of native a MYBPC gene (which corresponds to position 66 in SEQ ID No: 3 and position 38 in SEQ ID No: 4). Feline subjects are diagnosed as being at risk of developing familial hypertrophic cardiomyopathy when a mutation is detected in the polynucleotide encoding MYBPC. In some embodiments, these methods can include an additional step of amplifying all or a portion of the polynucleotide encoding MYBPC prior to the diagnosing step. In some embodiments, only those one or more exons suspected of containing the HC-causing mutation are selectively amplified.

Kits for Detecting the Presence or Absence of Mutations Associated with HC

In some embodiments, the present invention provides kits for identifying feline subjects who have or are at risk of developing HC. The kits contain in a first receptacle an aliquot of one or more polynucleotide probes specific for one or combinations of mutations. The kits may contain additional receptacles with aliquots of one or more different polynucleotide probes to the same or different mutations as the probes of the first receptacle. In some embodiments, the kits may contain one or more additional receptacles with aliquots of primers. The polynucleotide probe is completely hybridizable to DNA which encodes MYBPC and the primers are useful for amplifying DNA which encodes MYBPC.

Additional Methods for Detecting Mutations in MYBPC Associated With HC

Nucleic Acid Analyses

According to various embodiments of the invention, genetic material to be assessed can be obtained from any nucleated cell from the feline subject being tested. For assay of genomic DNA, virtually any biological sample (other than pure red blood cells) is suitable. For example, convenient tissue samples include whole blood, semen, saliva, skin and hair. For assay of cDNA or mRNA, the tissue sample must be obtained from cells in which the target nucleic acid is expressed, preferably from T lymphocytes.

According to various embodiments of the invention, the nucleotide which occupies a site of interest (e.g., nucleotide position 66 of exon 3 (codon 31), wherein there is a base change from G to C, which results in a corresponding change in the MYBPC protein sequence from Alanine (ALA) to Proline (PRO) can be identified by a variety methods, such as Southern analysis of genomic DNA; direct mutation analysis by restriction enzyme digestion; Northern analysis of RNA; denaturing high pressure liquid chromatography (DHPLC); gene isolation and sequencing; or hybridization of a specific oligonucleotide probe with amplified gene products. A sampling of suitable procedures is discussed below:

In some embodiments, probes may be used to hybridize to a segment of target DNA, for example, probes in which the mutation site aligns with a central position (e.g., in a 15-mer at the 7 position; in a 16-mer, at either the 8 or 9 position) of the probe. This design of probe achieves good discrimination in hybridization between different allelic forms. In one embodiment, probes specific for the G-C mutation at nucleotide position 66 in codon 31 of the Feline MYBPC gene may be used to identify one mutation shown in Maine Coon cats to be associated with HC.

According to some embodiments, the direct analysis of the sequence of a Feline MYBPC gene according to the present invention can be accomplished using either the dideoxy chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

In yet other embodiments, identification of a mutant form of the feline MYBPC gene is carried out using an oligonucleotide ligation assay (OLA), as described, e.g., in U.S. Pat. No. 4,998,617 and in Landegren, U. et al. ((1988) Science 241: 1077-1080). The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923-27). In this method, PCR is used to achieve the exponential amplification of target DNA, which is then detected using OLA.

Many of the methods described herein require amplification of DNA from target samples. The term "amplification" for purposes of this invention is intended to include any method or technique capable of increasing in number the respective DNA (including culturing) or RNA being discussed. This can be accomplished by e.g., PCR. See generally PCR Technology: Principles and Applications for DNA Amplification (ed. H. A. Erlich, Freeman Press, New York, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

A commonly used amplification technique is the polymerase chain reaction (PCR) which is an art recognized technique. Amplification products generated using the polymerase chain reaction can be analyzed by the use of denaturing gradient gel electrophoresis. Mutations can be identified based on the different sequence-dependent melting properties and electrophoretic migration of DNA in solution. Erlich, ed., PCR Technology, Principles and Applications for DNA Amplification, (W. H. Freeman and Co, New York, 1992), Chapter 7.

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

According to some embodiments, the presence or absence of a mutation associated with HC in the RNA is detected by preparing MYBPC cDNA from the RNA and detecting mutations in the DNA. In some embodiments, the MYBPC DNA can be amplified prior to detecting a mutation. RNA can be isolated from nucleated blood cells. Nucleated blood cells include lymphocytes, e.g. T and B cells, monocytes, and polymorphonuclear leukocytes. The RNA can be isolated using conventional techniques such as isolation from tissue culture cells, guantidinium methods and the phenol/SDS method. See Ausebel et al. (Current Protocols in Molecular Biology (1991), Chapter 4, Sections 4.1-4.3), the contents of which are expressly incorporated by reference.

"cDNA" means a DNA prepared using messenger RNA (mRNA) as a template. In contrast to genomic DNA and DNA polymerized from a genomic, non- or partially-processed RNA template, cDNA contains coding sequences of the corresponding protein in the absence of introns and other non-translated nucleic acids.

"Gene" refers broadly to any region or segment of DNA associated with a biological molecule or function. Thus, genes include coding sequence, and may further include regulatory regions or segments required for their expression. Genes may also include non-expressed DNA segments that, for example, form recognition sequences for other proteins. Genes can be obtained from a variety of sources, including cloning from a source of interest, or synthesizing from known or predicted sequence information, and may include sequences encoding desired parameters.

"Nucleic acid" and "polynucleotide" refer to deoxyribonucleotides or ribonucleotides, nucleotides, oligonucleotides, polynucleotide polymers and fragments thereof in either single- or double-stranded form. A nucleic acid may be of natural or synthetic origin, double-stranded or single-stranded, and separate from or combined with carbohydrate, lipids, protein, other nucleic acids, or other materials, and may perform a particular activity such as transformation or form a useful composition such as a peptide nucleic acid (PNA). Unless specifically limited, the term encompasses nucleic acids containing known analogues of natural nucleotides that have similar binding properties as the reference nucleic acid and may be metabolized in a manner similar to naturally-occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19: 5081; Ohtsuka et al. (1985) J. Biol. Chem. 260: 2605-2608; Cassol et al. (1992); Rossolini et al. (1994) Mol. Cell. Probes 8: 91-98). The term nucleic acid is used interchangeably with gene, cDNA, and mRNA encoded by a gene.

EXAMPLES

Clinical Description

The pedigree of the cats in the colony studied have been published previously. We evaluated twenty three related Maine Coon cats from this colony and 50 unaffected mixed breed control cats. Disease status was identified through repeated echocardiographic examinations. The median left ventricular (LV) wall thickness and interventricular wall thickness was 7 mm (range: 6-9 mm; normal=3 to 5 mm) in affected (n=16) cats.

Identification Of A MYBPC Mutation

Figure 4:
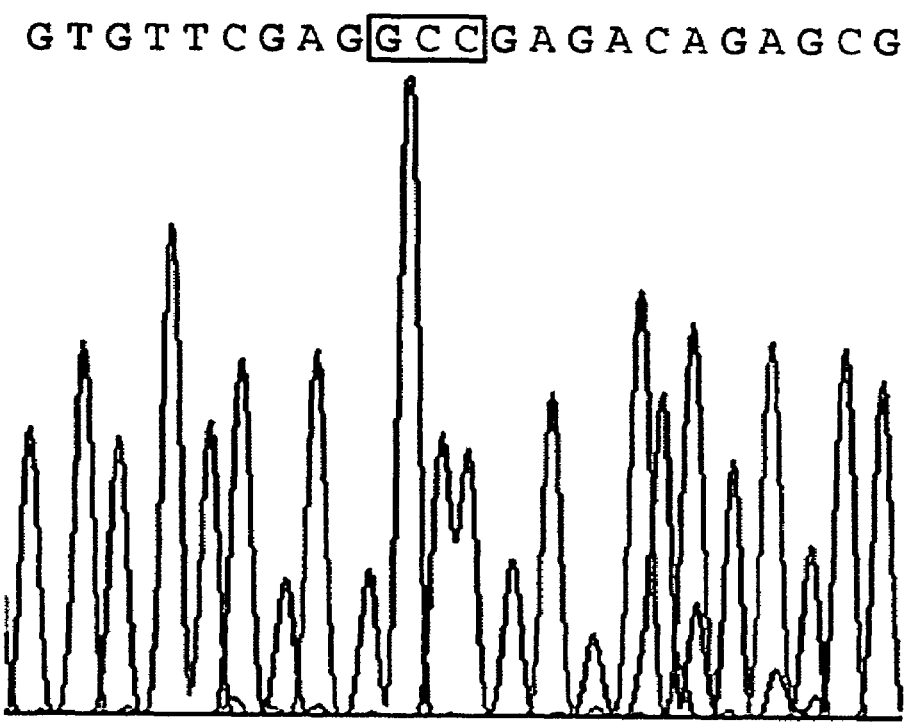
FIG. 4 shows DNA sequencing which identified a single base pair change (G to C) in codon 31 of the MYBPC3 gene in the affected cats (n=16) but not in any of the unaffected family members (n=7) or control cats (n=100). A homozygous affected cat is displayed.
Figure 4:
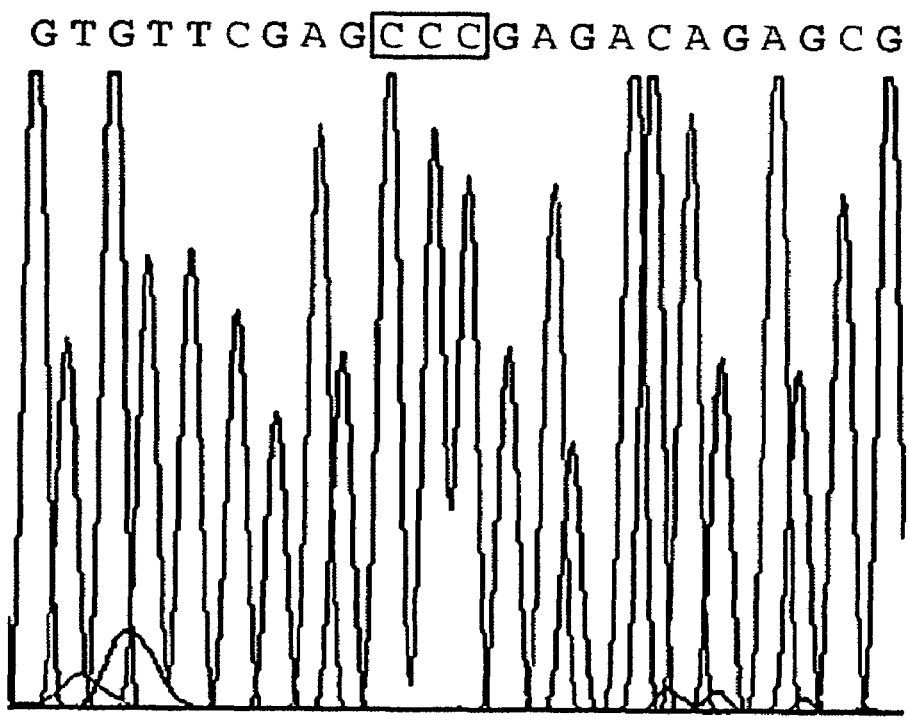
Figure 5:
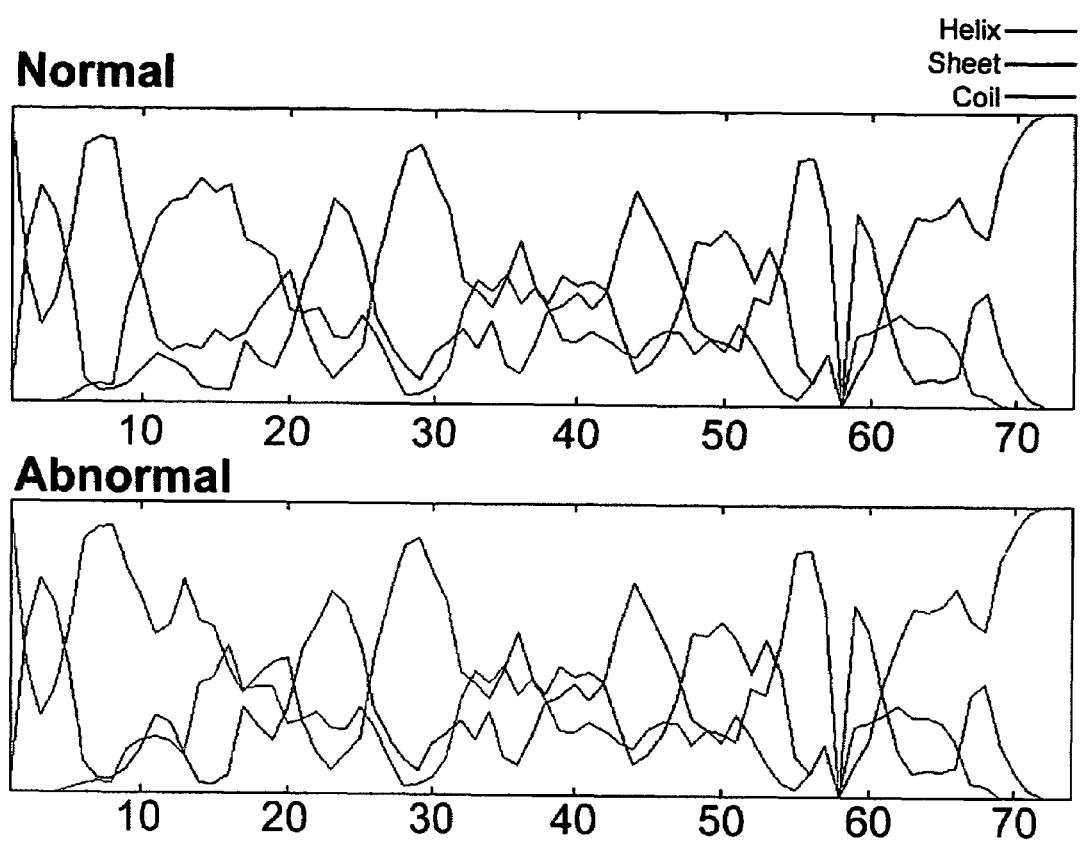
FIG. 5 shows a computer protein structure analysis which predicted a reduction in the alpha helix (blue) and an increase in random coils (purple) in the amino acid region from 10 to 20 (altered amino acid is 16) of the molecule in affected cats compared to normal cats.

DNA was extracted from peripheral lymphocytes isolated from each of the cats and the 38 coding exons of the MYBPC gene were amplified, using oligonucleotides designed to the published human gene sequence. DNA sequencing revealed a single base pair change (G to C) in codon 31 (G-C66) in affected cats. (see FIG. 4). This changes a conserved alanine (ALA) to proline (PRO) (A31P) in each of the Maine Coon cats with HCM but none of the unaffected Maine Coon or control cats. Affected cats were either heterozygous (n=10) or homozygous (n=6) for the mutation based on direct DNA sequence analysis. Computer protein structure analysis predicted a reduction in the alpha helix and an increase in random coils in this region of the molecule. (see FIG. 5).

Sarcomeric Protein Concentrations are Altered

LV myocardial samples were obtained from 8 affected cats at the time of death and from 3 healthy unrelated cats and evaluated proteins isolated from the myocardial samples by sodium dodecyl sulphate-polyacrylamide gel electrophoresis (SDS-PAGE) analysis. Two proteins were absent or greatly reduced and one was increased in the affected cats in comparison to the normal cats. The proteins reduced in the affected cats were identified by MALDI mass spectrometry (Ohio State Mass Spectrometry and Proteomics, Columbus, Ohio) as MYBPC and myomesin, an M band protein. The protein that was increased in the affected cats was identified as anomalously migrating beta myosin. (see FIG. 1). Western blot analysis confirmed the identification of all 3 proteins. When evaluated quantitatively by densitometry, both the MYBPC and myomesin proteins were significantly reduced in the affected cats in comparison to the control cats (MYBPC, p<0.001 and myomesin, p=0.011). A weak inverse correlation (r=−0.341) was observed between the amount of anomalously migrating myosin and the MYBPC for affected cats.

Sarcomeric Protein Organization is Altered

Figures 6A, 6B:
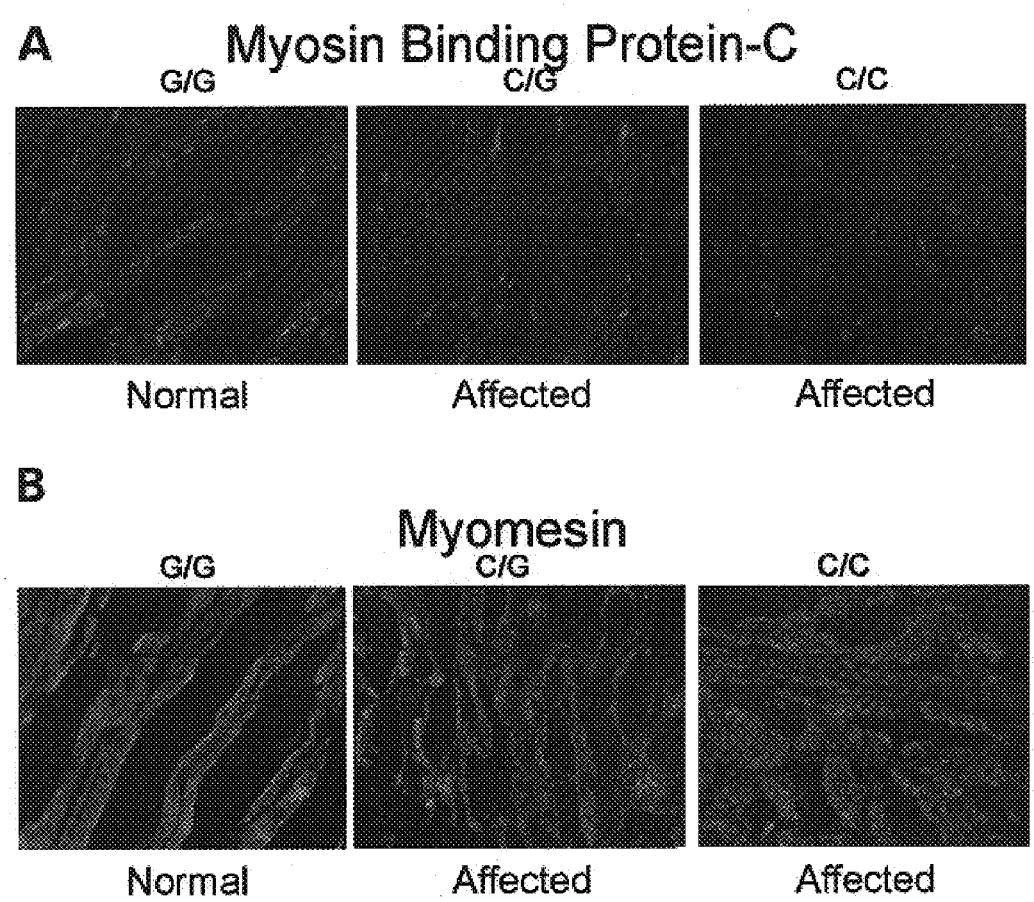
FIGS. 6A-6E show immunofluorescent staining of left ventricular free wall sections from affected and unaffected cats. Analysis of sarcomeric proteins in left ventricular sections from affected and unaffected cats revealed significant disruption to several sarcomeric proteins, with reductions in staining intensity of cMYBPC (A), myomesin (B), cardiac actin (C) and titin (D) in affected cats. However, staining for myosin heavy chain (E) and connexin 43 (data not shown) were normal. Proteins of interest are stained green, while phalloidin and DAPI staining are red and blue, respectively.
Figures 6C, 6D, 6E:
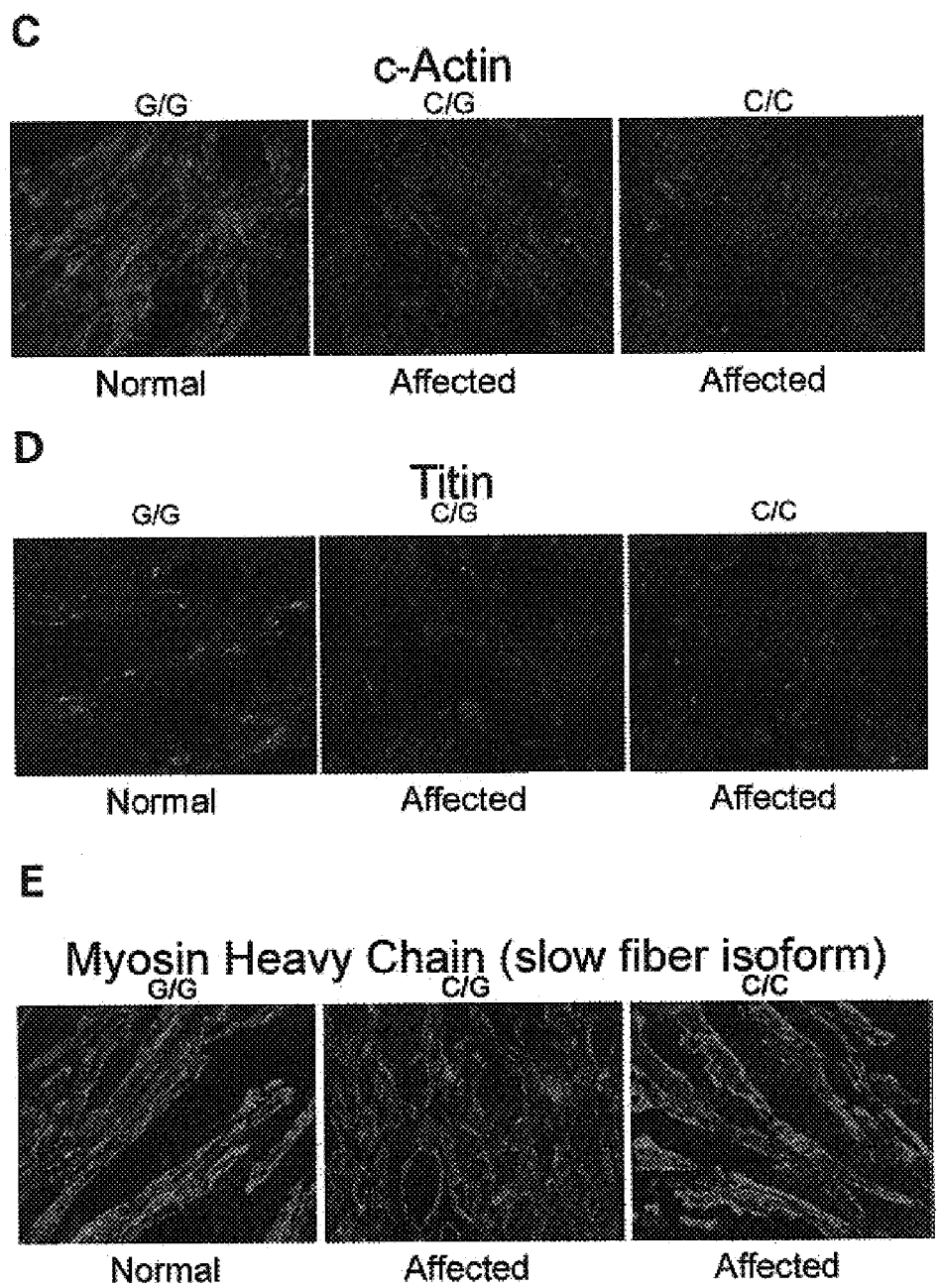
Figure 7:
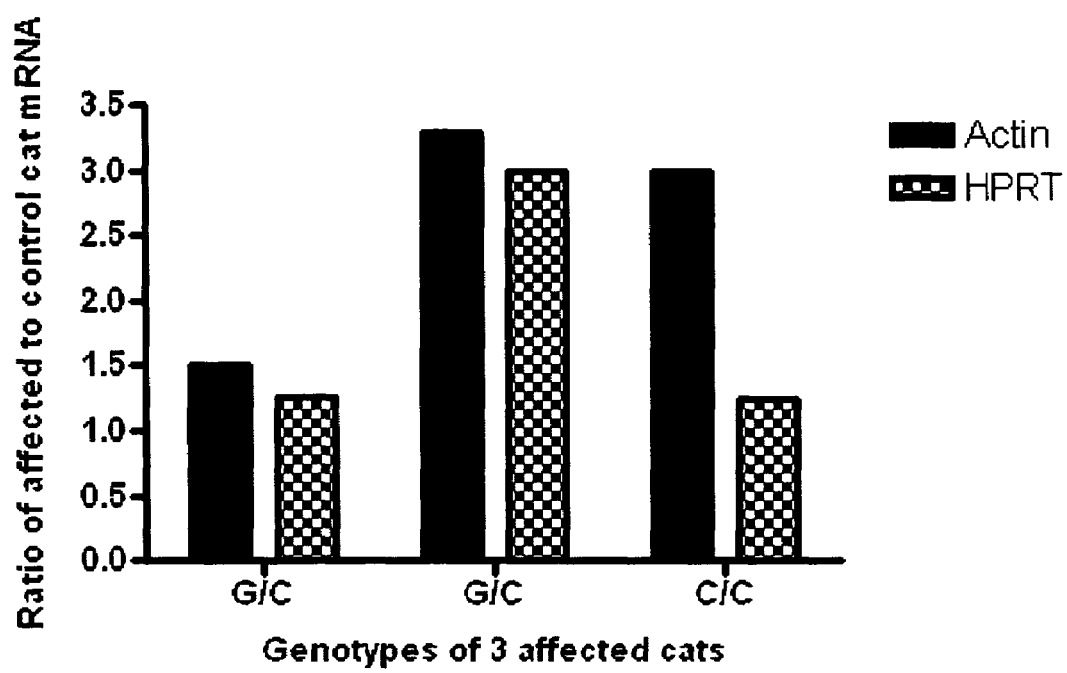
FIG. 7 shows a histogram of the ratio of MYBPC3 message RNA for three affected cats (two heterozygous and one homozygous) to three unaffected cats demonstrating that the amount of message RNA was increased 1.25-3-fold in affected cats. The HPRT and feline actin genes were used as housekeeping genes.

Immunofluorescence analysis of sarcomeric proteins in left ventricular sections from affected and unaffected cats revealed significant disruption in several sarcomeric proteins in affected cats, with reductions in staining intensity of MYBPC, myomesin, titin and cardiac actin. (see FIGS. 6A-6D) Staining for myosin heavy chain (see FIG. 6E) and connexin 43 (data not shown) were normal.

MYBPC mRNA is Increased

Although the MYBPC protein was noted to be reduced by SDS-PAGE, Western blot analysis, and immunofluorescence, real time PCR in 3 affected cats and 3 unaffected cats determined that the amount of mRNA in affected cats was increased 2-3 fold. This increase in message produced in conjunction with a decrease in protein may suggest either an inability to make the protein or increased protein degradation.

Disease Outcome Relates to Genotype

The phenotype of the affected cats evaluated in this study varied from moderate to severe HCM in cats whether they had one or two affected alleles. Disease outcome, however, related to the homozygosity or heterozygosity of the mutation. Five of the 6 cats with a homozygous mutation developed moderate to severe disease and died of their disease at 4 years of age or less, 4 of them suddenly. One of these cats appeared echocardiographically normal but died unexpectedly under anesthesia at 4 years of age. In comparison, 3 of the 10 cats with a heterozygous mutation are still alive at 8 to 12 years of age with moderate disease and only one died suddenly, although five developed severe HCM and died of heart failure. One of these cats had severe HCM by 2 years of age and throughout life but died of heart failure due to dilated cardiomyopathy at 5 years of age. One died of an unrelated cause. Most of the cats had echocardiographic evidence of HCM by two to three years of age but one female (heterozygote) did not have echocardiographically identifiable disease until 7 years of age.

Discussion

In this study, a MYBPC mutation was identified in a purebred domestic cat model of familial HCM. This is the first known spontaneous cause of familial HCM identified in a species other than *Homo sapiens*. The missense mutation reported in this feline model is located in the linker region between domains C0 and C1 of the protein. The functional aspects of this area are not well understood, however there is evidence that domain C0 and the C0-C1 linker region bind to myosin and/or actin. The observation that the mutation identified in this model changes the computed structure of this protein in this region may affect its interaction with these cardiac proteins.

Both the MYBPC and myomesin proteins were decreased in the myocardium of affected cats in this study although the causative mutation was observed in the MYBPC gene. Additionally a proportion of myosin migrated anomalously. The abnormal behavior of the two additional proteins is likely due to the significant interactions observed between them. Myomesin is a smaller (185 kilodaltons) anchoring protein in the M-band that interacts with both titin and myosin in the assembly and stabilization of myofibrils. Both myomesin and the MYBPC are built into the cytoskeletal lattice with titin before myosin, even though the sarcomeric myosin heavy chain is one of the first myofibrillar proteins expressed. It could be hypothesized that myomesin was partially degraded in these cats due to failure to be properly incorporated into the sarcomeric complex. The correct assembly of this cytoskeletal scaffold appears to be an important prerequisite for correct thick filament assembly and the integration of the contractile apparatus into the myofibril. The immunohistochemical analyses suggest that this mutation leads to disruption of the scaffold, as indicated by the aberrant staining of myomesin and titin in addition to MYBPC, but does not prevent the integration of the myosin heavy chain into the sarcomeric organization, despite the fact that this integration of the preformed myosin filaments occurs only after the assembly of titin and myomesin into M bands and MYBPC into the A bands. However, although MYBPC protein is not needed for formation of myosin filaments, it has been previously suggested that it is probably needed for them to form normally, since without the normal content of MYBPC protein, synthetic myosin filaments were observed to be thicker and longer and to have a more heterogeneous thickness. While these data are not supported by the analyses reported herein, this may explain the anomalous migration of the myosin detected by SDS-PAGE. Such aberrant electrophoretic mobility of a protein on a SDS-PAGE has been observed for proteins that undergo post translational modifications. The mechanism for the anomalous migration of myosin in this study is unclear, but it might be speculated that the reduced or abnormal MYBPC protein prevented normal formation and integration of a proportion of the myosin into the thick filaments and that myosin that is not integrated normally may migrate anomalously. However, sufficient unaffected myosin remained to be detected by immunohistochemistry.

The identification of the first sarcomeric gene mutation in a non human species is highly significant and completes the development of this animal model of familial HCM. Our findings should increase the ability of investigators to use this model to address some of the remaining questions regarding HCM such as the mechanism by which this specific mutation leads to the development of hypertrophy, the effect of modifiers on clinical phenotype and prognosis, and the optimal effects of therapy on these variables. Additionally, evaluation of this model with a unique mutation within the domain 0-1 linker may aid in providing information about the structure and function of this domain.

Methods

This study was conducted in accordance with the "Position of the American Heart Association on Research and Animal Use" and under the guidelines of the Animal Care and Use Committee of the University of California at Davis.

Animal Procurement and Determination of Phenotypic Expression

Twenty three (16 affected, 7 unaffected) Maine Coon cats from a colony with familial HCM, as previously described, and 50 unaffected control cats were evaluated. Disease status of adult cats was identified through repeated echocardiographic examinations. Feline echocardiographic studies were performed using an Acuson 128XP/10 ultrasound machine (Siemens, Malvern, Pa.) and a 7-MHz transducer using standard views. Cats were diagnosed with HCM when severe papillary muscle hypertrophy was present and one or more regions of the LV wall were $\geq 6.0$ mm thick. Most affected cats also had systolic anterior motion of the mitral valve and left atrial enlargement.

SDS PAGE Analysis and Immunoblotting

Myocardial samples were obtained from eight cats at the time of death due to euthanasia for refractory heart failure, or as soon after death as possible from cats that died suddenly as well as from 3 apparently healthy unrelated cats. The preparation of protein samples and methods for preparing gels and the running conditions were as described previously by Reiser and Kline. Stacking gels consisted of 4% total acrylamide (acrylamide:bis=50:1) and 5% (v/v) glycerol (pH 6.8). Separating gels consisted of 7% total acrylamide (acrylamide:bis=50:1) and 5% (v/v) glycerol (pH 8.8). Protein loads were ~12 μg per gel lane. The gels were run in a Hoefer SE600 unit at 250 constant volts for 15 hours at 8° C. A set of molecular weight standards was loaded in one lane to verify the identification of the MHC bands. After electrophoresis, the gels were silver-stained and evaluated by densitometry for quantitation of the specific proteins. Protein bands of interest were evaluated by loading gels with ~20× more total protein, staining the gel with Coomassie blue and analyzing the excised bands by MALDI mass spectrometry.

Immunoblotting was performed to identify the proteins (MYBPC, myomesin, myosin heavy chain) of interest in the stained gels. Proteins were separated by SDS-PAGE (as described above) and transferred to nitrocellulose. Blots were incubated with an anti-myosin heavy chain antibody (MF 20, Developmental Studied Hybridoma Bank, University of Iowa, Iowa City, Iowa) diluted at 1:50, a rabbit polyclonal anti-rat myosin binding protein C antibody (gift from Dr. Samantha Harris, University of Wisconsin, Madison, Wis.) at 1:500 dilution or a mouse monoclonal anti-chicken myomesin antibody B4 (1:500 dilution) (gift from Dr. H. M. Eppenberger, Institut für Zellbiologie, ETH-Zürich, Switzerland). The blots were washed with TBST three times, incubated with an anti-mouse alkaline phosphatase-conjugated secondary antibody (1:6667 dilution, Promega, Madison, Wis.) and washed again three times with TBST. Color development was performed with NBT and BCIP (Promega) as substrates.

Mutation Analysis

DNA was extracted from peripheral lymphocytes from all cats as previously described. Oligonucleotides were designed for amplification of exons of several feline sarcomeric genes, including the Feline MYBPC gene, using known human sequences (GenBank U91629) and Primer3 software. Annealing temperatures were optimized for each exon and individual exons were amplified at 95° C. (5 minutes) followed by 40 cycles of 94° C. (20 secs), optimized annealing temperature (20 secs), and 74° C. (39 secs). Amplified samples were sequenced using an ABI377 (Applied Biosystems, Foster City, Calif.) sequencer and compared for base pair changes. Sequences were analyzed for species conservation (mouse, rat, human) by comparison with sequences published in GenBank.

Structural Analysis

Protein structure predictions were performed using the GOR4 (PBIL, France) and the Protein Structure Analysis software programs. (BMERC, Boston, Mass.).

Immunohistochemistry

Frozen myocardial sections (7 μm) were cut from the left ventricle. Unfixed sections were stained, using MYBPC (gift from Dr. Samantha Harris, University of Wisconsin, Madison, Wis.), myomesin (gift from Dr. H. M. Eppenberger, Institut für Zellbiologie, ETH-Zürich, Switzerland), actinin-2 (Clone Ea-53, Sigma-A7811), myosin (clone NOQ7.5.4D, Sigma M8421), connexin-43 (clone CXN-6, Sigma C8093), and cardiac actin (clone AC-40, Sigma A4700) antibodies. Each primary antibody was diluted 1:500 in PBS pH 7.2 containing 5% BSA and then added to the sections: these were incubated for 1 hour at room temperature. The slides were washed for 10 minutes three times in 1×PBS pH 7.2 at room temperature. The sections were then incubated with secondary antibody (Alexa-488—anti-mouse conjugated secondary antibody. Molecular probes), diluted 1:1000 in PBS pH 7.2 containing 5% BSA, for 1 hour at room temperature. The slides were washed three times in 0.1×PBS pH 7.2 and mounted with Cytoseal™280 mounting medium (Stephens Scientific, Riverdale, N.J.), prior to observation.

Real Time PCR

Messenger RNA was purified and quantitated from left ventricular myocardial samples of 3 affected and 3 unaffected cats with a Quickprep Micro mRNA purification kit (Amersham Bioscience, Piscataway, N.J.).

Single step reverse transcription and real-time PCR was performed on purified mRNA, using probes designed to be complementary to a segment located in exon 22 of MYBPC (F-AACCTCCCAAGATCCACCTGG, SEQ ID No: 1, R-CTGCGTGATAGCCTTCTGCC, SEQ ID No: 2) and the feline actin gene (GenBank AB005557) as a housekeeping gene as previously described. In brief, a mixture of all reagents required for RT-PCR was prepared to equal a total concentration of 25 µl: 12.5 µl SYBR green reaction buffer (Qiagen, Valencia, Calif.), 10 µl RNase-free water, 0.65 µl 20 µM forward primer, 0.65 µl 20 µM reverse primer, 2.0 µl purified mRNA (≦250 ng/reaction) and 0.25 µl reverse transcriptase. Samples were run in triplicate on a Stratagene Mx3000P (Stratagene, La Jolla, Calif.) in 96-well MicroAmp optical plates (Applied Biosystems, Foster City, Calif.). Reverse transcription was performed at 50° C. for 30 minutes, followed by inactivation of the reverse transcriptase at 95° C. for 15 minutes, and 40 cycles of 94° C. (15 seconds), 57° C. (30 seconds), 72° C. (30 secs). Relative quantities were calculated using the Stratagene instrument software.

Statistical Analysis

The Student's t-test was used to evaluate differences in protein quantity between affected and unaffected cats. A Pearson correlation was used to determine a correlation between quantity of MYBPC and anomalously migrating myosin. Significance was defined as an alpha of <0.05.

We claim:

1. A method for diagnosing feline hypertrophic cardiomyopathy or predicting the likelihood that a feline of the breed Maine Coon cat will develop hypertrophic cardiomyopathy comprising:

a) obtaining a nucleic acid sample from the feline of the breed Maine Coon cat to be assessed;

b) detecting in the nucleic acid sample a polynucleotide that encodes MYBPC and has a sequence as set forth in SEQ ID NO: 3, and determining whether the MYBPC polynucleotide has a cytosine at position 66 of SEQ ID NO: 3, wherein the presence of a cytosine at position 66 in SEQ ID NO: 3 indicates that the feline has feline hypertrophic cardiomyopathy or has a greater likelihood of developing feline hypertrophic cardiomyopathy than a feline having a guanine at position 66 in SEQ ID NO: 3.

2. The method according to claim 1, wherein detecting in the nucleic acid sample a polynucleotide that encodes MYBPC and has a sequence as set forth in SEQ ID NO:3, and determining whether the MYBPC polynucleotide has a cytosine at position 66 of SEQ ID NO:3 comprises providing a primer set for amplifying a fragment of genomic DNA from a feline of the breed Maine Coon cat comprising:

a) a forward primer, capable of hybridizing to a contiguous sequence of nucleotides in that part of the polynucleotide that encodes MYBPC that is 5' of position 66 of SEQ ID NO:3; and b) a reverse primer, capable of hybridizing to a contiguous sequence of nucleotides in that part of the polynucleotide that encodes MYBPC that is 3' of position 66 of SEQ ID NO:3.

3. The method according to claim 2, wherein each primer has a length from about 10 to 30 nucleotides.

4. The method according to claim 2, wherein each primer has a length from about 15 to 25 nucleotides.

5. The method according to claim 2, wherein each primer has a length from about 18 to 22 nucleotides.

6. The method according to claim 1, wherein detecting in the nucleic acid sample a polynucleotide that encodes MYBPC and has a sequence as set forth in SEQ ID NO:3, and determining whether the MYBPC polynucleotide has a cytosine at position 66 of SEQ ID NO:3 comprises providing a polynucleotide probe capable of hybridizing under stringent conditions to a region within the polynucleotide that encodes MYBPC that comprises position 66 of SEQ ID NO:3.

7. The method according to claim 6, wherein the polynucleotide probe has a length from about 14 to 80 nucleotides.

8. The method according to claim 6, wherein the polynucleotide probe has a length from about 15 to 20 nucleotides.

9. The method according to claim 1, wherein detecting in the nucleic acid sample a polynucleotide that encodes MYBPC and has a sequence as set forth in SEQ ID NO:3, and determining whether the MYBPC polynucleotide has a cytosine at position 66 of SEQ ID NO:3 comprises:

a) providing a primer set for amplifying a fragment of genomic DNA from a feline subject comprising:

1) a forward primer, capable of hybridizing to a contiguous sequence of nucleotides in that part of the polynucleotide that encodes MYBPC that is 5' of position 66 of SEQ ID NO:3, and 2) a reverse primer, capable of hybridizing to a contiguous sequence of nucleotides in that part of the polynucleotide that encodes MYBPC that is 3' of position 66 of SEQ ID NO:3; and b) providing a polynucleotide probe capable of hybridizing under stringent conditions to a region within the polynucleotide that encodes MYBPC that comprises position 66 of SEQ ID NO:3.

* * * * *

SEQUENCE LISTING

```
<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
aacctcccaa gatccacctg g                                        21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ctgcgtgata gccttctgcc                                          20

<210> SEQ ID NO 3
<211> LENGTH: 268
<212> TYPE: DNA
<213> ORGANISM: Unknown Organism
<220> FEATURE:
<223> OTHER INFORMATION: Description of Unknown Organism: Feline
      sequence

<400> SEQUENCE: 3
tctcagcctt tagcaagaag ccaaggtcag tggaagtggc agccagcagc tctgctgtgt    60
tcgaggccga gacagagcgg tcaggagtaa aggtgcgctg gcagcggggg ggcagtgaca   120
tcagcgccag tgacaagtat ggcctagcag ccgagggcac tgaggcacac tctgacagtg   180
cgggacgtgg gccccaccga ccagggaccc tacgcagtca tcgctggctc ctccaaggtc   240
aagtttgacc tcaaggtcat agaagcag                                     268

<210> SEQ ID NO 4
<211> LENGTH: 229
<212> TYPE: DNA
```

```
<213> ORGANISM: Unknown Organism
<220> FEATURE:
<223> OTHER INFORMATION: Description of Unknown Organism: Feline
      sequence
<220> FEATURE:
<221> NAME/KEY: modified_base
<222> LOCATION: (78)..(84)
<223> OTHER INFORMATION: a, c, g, t, unknown or other

<400> SEQUENCE: 4
agtggaagtg gcagccagca gctctgctgt gttcgaggcc gagacagagc ggtcaggagt    60
aaaggtgcgc tggcagcnnn nnnncagtga catcagcgcc agtgacaagt atggcctagc   120
agccgagggc actgaggcac actctgacag tgcgggacgt gggccccacc gaccagggac   180
cctacgcagt catcgctggc tcctccaagg tcaagtttga cctcaaggt              229

<210> SEQ ID NO 5
<211> LENGTH: 268
<212> TYPE: DNA
<213> ORGANISM: Unknown Organism
<220> FEATURE:
<223> OTHER INFORMATION: Description of Unknown Organism: Feline
      sequence

<400> SEQUENCE: 5
tctcagcctt tagcaagaag ccaaggtcag tggaagtggc agccagcagc tctgctgtgt    60
tcgaggccga gacagagcgg tcaggagtaa aggtgcgctg gcagcggggg ggcagtgaca   120
tcagcgccag tgacaagtat ggcctagcag ccgagggcac tgaggcacac tctgacagtg   180
cgggacgtgg gccccaccga ccagggaccc tacgcagtca tcgctggctc ctccaaggtc   240
aagtttgacc tcaaggtcat agaagcag                                     268

<210> SEQ ID NO 6
<211> LENGTH: 339
<212> TYPE: DNA
<213> ORGANISM: Unknown Organism
<220> FEATURE:
<223> OTHER INFORMATION: Description of Unknown Organism: Feline
      sequence

<400> SEQUENCE: 6
gtaagaccct ggtccgcctt ccctaggttt gagcttctgg ggcagcctgg ccatctctcc    60
ctcacccagg gtataggagg agcctttcca ctgtctcgcc tttgctttgg ctgagccgtc   120
tgccaggaat tcccttcctc ccttttctgc agcaagacct cactgagtgt ccccatgtgt   180
ctccctggcc tgttccagtc atccagggta taggaggagc ctttccactg tctcgccttt   240
gctttggctg agccgtctgc caggaattcc cttcctccct tttctgcagc aagacctcac   300
tgagtgtccc catgtgtctc cctggcctgt tccagtcat                         339

<210> SEQ ID NO 7
<211> LENGTH: 116
<212> TYPE: DNA
<213> ORGANISM: Unknown Organism
<220> FEATURE:
<223> OTHER INFORMATION: Description of Unknown Organism: Feline
      sequence

<400> SEQUENCE: 7
agagaaggca gagcctgtgc cgggccctgc tcctgcccct actgaggctc ctggaggctc    60
cggagaagca ctgacctcga ccactgagga ggaaggaggc tccccaagtc ccaaag      116
```

```
<210> SEQ ID NO 8
<211> LENGTH: 92
<212> TYPE: DNA
<213> ORGANISM: Unknown Organism
<220> FEATURE:
<223> OTHER INFORMATION: Description of Unknown Organism: Feline
      sequence

<400> SEQUENCE: 8
gtcaagttca gcagccccg atggctctgg tgcctctgat gacccccatcg gcctctttgt    60 gatgcggcca caggatggcg aggtgaccgt gg                                  92

<210> SEQ ID NO 9
<211> LENGTH: 362
<212> TYPE: DNA
<213> ORGANISM: Unknown Organism
<220> FEATURE:
<223> OTHER INFORMATION: Description of Unknown Organism: Feline
      sequence

<400> SEQUENCE: 9
gtggctgcat caccttctca gcccgcgtgg ccggcgccag cctcctgaaa ccgcccacag    60
tcaagtggtt caagggcaag tgggtggacc tgagcagcaa ggtgggccaa cacctgcagc   120
tgcacaacag ttacgaccgg accagcaagg gtggacctga gcagcaaggt gggccaacac   180
ctgcagctgc acaacagtta cgaccggacc agcaaggtac cttgctggtc cggtcgtaac   240
tgttgtgcag ctgcaggtgt tggcccacct tgctgctcag gtccaccac ttgcccttga    300 accacttgac tgtgggcggt tcaggaggc tggcgccggc cacgcgggct gagaaggtga    360
tg                                                                  362

<210> SEQ ID NO 10
<211> LENGTH: 118
<212> TYPE: DNA
<213> ORGANISM: Unknown Organism
<220> FEATURE:
<223> OTHER INFORMATION: Description of Unknown Organism: Feline
      sequence

<400> SEQUENCE: 10
gtctacctgt ttgagctgca cattacagat gcccagacta ctttcgcagg tggctaccgc    60
tgtgaggttt ccaccaagga caaatttgac agctgcaact tcagtctcac tgtccatg    118

<210> SEQ ID NO 11
<211> LENGTH: 221
<212> TYPE: DNA
<213> ORGANISM: Unknown Organism
<220> FEATURE:
<223> OTHER INFORMATION: Description of Unknown Organism: Feline
      sequence

<400> SEQUENCE: 11
gtgaggggag ccctggcgtc ctgggctcag gtccccatgg gtcttatccc ccacgtctgc    60
ctccatttcc caacactaag gaggatgtct agtcccaaca ggacaaccgc tgcccacatg   120
cccagtgctg ctcatgcagg gggaaaggct cagaatgtgg ggtcctgggg cagatgcccc   180
ctctcaaggg tcatggatgg gcaggtctgt tgaacgcaga g                       221

<210> SEQ ID NO 12
<211> LENGTH: 47
<212> TYPE: DNA
<213> ORGANISM: Unknown Organism
<220> FEATURE:
```

```
<223> OTHER INFORMATION: Description of Unknown Organism: Feline
      sequence

<400> SEQUENCE: 12
gccgttggcc ctggagacct ggacctccga tcagctttcc gccgcac                    47

<210> SEQ ID NO 13
<211> LENGTH: 67
<212> TYPE: DNA
<213> ORGANISM: Unknown Organism
<220> FEATURE:
<223> OTHER INFORMATION: Description of Unknown Organism: Feline
      sequence

<400> SEQUENCE: 13
gtgagtggtc atctcttctc agggacggcg gggaggccag tgctgggatc tgaagcccct     60
cggggtc                                                                67

<210> SEQ ID NO 14
<211> LENGTH: 30
<212> TYPE: DNA
<213> ORGANISM: Unknown Organism
<220> FEATURE:
<223> OTHER INFORMATION: Description of Unknown Organism: Feline
      sequence

<400> SEQUENCE: 14
gagcctggct ggaagtggtc ggcggatcag                                       30

<210> SEQ ID NO 15
<211> LENGTH: 55
<212> TYPE: DNA
<213> ORGANISM: Unknown Organism
<220> FEATURE:
<223> OTHER INFORMATION: Description of Unknown Organism: Feline
      sequence

<400> SEQUENCE: 15
gtgacagcca cgaggacgct ggaactctgg atttcagctc gctgctgaag aagag          55

<210> SEQ ID NO 16
<211> LENGTH: 18
<212> TYPE: DNA
<213> ORGANISM: Unknown Organism
<220> FEATURE:
<223> OTHER INFORMATION: Description of Unknown Organism: Feline
      sequence

<400> SEQUENCE: 16
cagtttccgg aacctaag                                                    18

<210> SEQ ID NO 17
<211> LENGTH: 157
<212> TYPE: DNA
<213> ORGANISM: Unknown Organism
<220> FEATURE:
<223> OTHER INFORMATION: Description of Unknown Organism: Feline
      sequence

<400> SEQUENCE: 17
ggacccgagg ctggaggcgc cagccgagga ggacgtgtgg gagatcctgc ggcaggcatc     60
cccctccgaa tatgagcgca tcgccttcca gcacggcatc accgacctgc gtggcatgct    120
caagaggctc aagggcatga agcgagatga gaagaag                             157
```

```
<210> SEQ ID NO 18
<211> LENGTH: 133
<212> TYPE: DNA
<213> ORGANISM: Unknown Organism
<220> FEATURE:
<223> OTHER INFORMATION: Description of Unknown Organism: Feline
      sequence

<400> SEQUENCE: 18
cctttcagaa gaagctggag cccgcctacc aggtgagcaa gggccacaag atccggctga      60
ccgtggagct ggccgacccc gacgccgagg tcaagtggct gaagaatgga caggagatcc     120
agatgagcgg cag                                                        133

<210> SEQ ID NO 19
<211> LENGTH: 127
<212> TYPE: DNA
<213> ORGANISM: Unknown Organism
<220> FEATURE:
<223> OTHER INFORMATION: Description of Unknown Organism: Feline
      sequence
<220> FEATURE:
<221> NAME/KEY: modified_base
<222> LOCATION: (34)
<223> OTHER INFORMATION: a, c, g, t, unknown or other
<220> FEATURE:
<221> NAME/KEY: modified_base
<222> LOCATION: (38)
<223> OTHER INFORMATION: a, c, g, t, unknown or other
<220> FEATURE:
<221> NAME/KEY: modified_base
<222> LOCATION: (46)
<223> OTHER INFORMATION: a, c, g, t, unknown or other
<220> FEATURE:
<221> NAME/KEY: modified_base
<222> LOCATION: (90)..(97)
<223> OTHER INFORMATION: a, c, g, t, unknown or other
<220> FEATURE:
<221> NAME/KEY: modified_base
<222> LOCATION: (107)
<223> OTHER INFORMATION: a, c, g, t, unknown or other

<400> SEQUENCE: 19
gtacatcttc gagtccgtgg gtgccaagcg cacnctgnac catcanccag tgctcgctga      60
gccgatgacg cggcctacca gtgcgtggtn nnnnnnnaga agtgcantac cgagctgttc     120
gtcaaag                                                               127

<210> SEQ ID NO 20
<211> LENGTH: 109
<212> TYPE: DNA
<213> ORGANISM: Unknown Organism
<220> FEATURE:
<223> OTHER INFORMATION: Description of Unknown Organism: Feline
    sequence

<400> SEQUENCE: 20 agagccccc gtgctgatca ctcggcccct ggaagaccag ctggtgatgg tggggcagcg       60
ggtggagttt gagtgcgaag tgtctgagga gggggcccag gtcaagtgg                 109

<210> SEQ ID NO 21
<211> LENGTH: 169
<212> TYPE: DNA
<213> ORGANISM: Unknown Organism
<220> FEATURE:
<223> OTHER INFORMATION: Description of Unknown Organism: Feline
      sequence
<220> FEATURE:
<221> NAME/KEY: modified_base
<222> LOCATION: (121)
```

<223> OTHER INFORMATION: a, c, g, t, unknown or other

<400> SEQUENCE: 21

```
ggctgaagga tggggtggag ctgaccaggg aggagacctt caaataccgg ttcaagaagg    60
acgggcagag acaccacctc atcatcaact aggcgatcgc tggaggacgc ggggcactac   120
ncgctgcgca ccagcggggg ccaggcgctg gccgagctca tcgttcagg              169
```

<210> SEQ ID NO 22
<211> LENGTH: 166
<212> TYPE: DNA
<213> ORGANISM: Unknown Organism
<220> FEATURE:
<223> OTHER INFORMATION: Description of Unknown Organism: Feline sequence

<400> SEQUENCE: 22

```
aaaagaagct ggaggtgtac cagagcatcg cagacctgac cgtgggtgca aaggaccagg    60
cggtgttcaa gtgtgaagtg tccgatgaga acgtgcgggg cgtgtggctg aagaacggga   120
aggagctggt gcccgacagc cgcgtgaagg tgtcccacat tgggcg                  166
```

<210> SEQ ID NO 23
<211> LENGTH: 107
<212> TYPE: DNA
<213> ORGANISM: Unknown Organism
<220> FEATURE:
<223> OTHER INFORMATION: Description of Unknown Organism: Feline sequence

<400> SEQUENCE: 23

```
agtccacaaa ctgaccattg acgacgtcac gcctgccgac gaggcggact acagctttgt    60
gcctgagggc ttcgcctgca acctgtcagc gaaactccat ttcatgg                 107
```

<210> SEQ ID NO 24
<211> LENGTH: 31
<212> TYPE: DNA
<213> ORGANISM: Unknown Organism
<220> FEATURE:
<223> OTHER INFORMATION: Description of Unknown Organism: Feline sequence

<400> SEQUENCE: 24

```
gaggtcaaga ttgacttcgt gcccaggcaa g                                   31
```

<210> SEQ ID NO 25
<211> LENGTH: 142
<212> TYPE: DNA
<213> ORGANISM: Unknown Organism
<220> FEATURE:
<223> OTHER INFORMATION: Description of Unknown Organism: Feline sequence

<400> SEQUENCE: 25

```
agaacctccc aagatccacc tggactgccc gggccgcaag ccggatacca ttgtggttgt    60
ggctgggaac aagctacgcc tggatgtccc tatctctggg gaccctgctc ccactgtgat   120
ttggcagaag gctatcacgc ag                                            142
```

<210> SEQ ID NO 26
<211> LENGTH: 91
<212> TYPE: DNA
<213> ORGANISM: Unknown Organism
<220> FEATURE:
<223> OTHER INFORMATION: Description of Unknown Organism: Feline sequence
<220> FEATURE:
<221> NAME/KEY: modified_base
<222> LOCATION: (72)
<223> OTHER INFORMATION: a, c, g, t, unknown or other

<400> SEQUENCE: 26
gtactgtgga tccctcctcc acttccccat ctgtaaaatg ggtgtccagg ctgagtcagc    60
ccctcttccc cntgcttccc tccggctctg t                                  91

<210> SEQ ID NO 27
<211> LENGTH: 86
<212> TYPE: DNA
<213> ORGANISM: Unknown Organism
<220> FEATURE:
<223> OTHER INFORMATION: Description of Unknown Organism: Feline
      sequence

<400> SEQUENCE: 27
gaagaacaag gtcccagcag ggccatccct ggatgcccca ggggaggat gcaggtgaca     60 gtgacgagtg ggtgtttgac aagaag                                        86

<210> SEQ ID NO 28
<211> LENGTH: 161
<212> TYPE: DNA
<213> ORGANISM: Unknown Organism
<220> FEATURE:
<223> OTHER INFORMATION: Description of Unknown Organism: Feline
      sequence

<400> SEQUENCE: 28
gctgctgtgt gagaccgagg gccgggtgcg ggtggagacc accaaggacc gcagcatctt    60
cactgtcgag ggggcagaga aggaagacga gggtgtctac gttgtcacgg tgaagaaccc   120
cgtgggcgag gaccaggtca acctcacagt caaggtcatc g                       161

<210> SEQ ID NO 29
<211> LENGTH: 106
<212> TYPE: DNA
<213> ORGANISM: Unknown Organism
<220> FEATURE:
<223> OTHER INFORMATION: Description of Unknown Organism: Feline
      sequence

<400> SEQUENCE: 29
atgtgccaga tccccccgcg gcccccaaga tcagcaatgt gggtgaggac tcctgcaccg    60
tgcagtggga gccgcctgcc tacgacgggg gacagccagt cctggg                  106

<210> SEQ ID NO 30
<211> LENGTH: 190
<212> TYPE: DNA
<213> ORGANISM: Unknown Organism
<220> FEATURE:
<223> OTHER INFORMATION: Description of Unknown Organism: Feline
      sequence

<400> SEQUENCE: 30
ggctacatcc tggagcgcaa gaagaagaag agcttccggt ggatgcggct gaactttgac    60
ctgctgcagg agctgagcca cgaggcacgg cgcatgattg agggcgtggt gtatgagatg   120
cgagtctacg cggtcaatgc catcggcatg tccaggccca gccctgcctc ccagcccttc   180
atgcctattg                                                          190

```
<210> SEQ ID NO 31
<211> LENGTH: 137
<212> TYPE: DNA
<213> ORGANISM: Unknown Organism
<220> FEATURE:
<223> OTHER INFORMATION: Description of Unknown Organism: Feline
      sequence

<400> SEQUENCE: 31
ggccccccca gtgagcccac ccacctggcc gtggaggatg tctcagacac caccgtctcc     60
ctcaagtggc ggccccggga gcgggtggga gccggaggct tggatggcta cagcgtggag    120
tattgccggg agggctg                                                   137

<210> SEQ ID NO 32
<211> LENGTH: 168
<212> TYPE: DNA
<213> ORGANISM: Unknown Organism
<220> FEATURE:
<223> OTHER INFORMATION: Description of Unknown Organism: Feline
      sequence

<400> SEQUENCE: 32
gctcggagtg ggtagctgcc ctggaggggc tgacagaacg cacctcgttg ctggtgaagg     60
acctgcccac gggggcccgg ctgctcttcc gtgtgcgggc gcacaatatg gcggggcccg    120
gggcccccat cgccaccaag gagcccgtga cggtgcagga gatactgc                 168

<210> SEQ ID NO 33
<211> LENGTH: 90
<212> TYPE: DNA
<213> ORGANISM: Unknown Organism
<220> FEATURE:
<223> OTHER INFORMATION: Description of Unknown Organism: Feline
      sequence

<400> SEQUENCE: 33
gacggccacg gctccaggtg ccccggcacc tgcgccagac catccagagg aaggtcgggg     60
agcccgtgaa cctcctcatt cctttccagg                                     90

<210> SEQ ID NO 34
<211> LENGTH: 198
<212> TYPE: DNA
<213> ORGANISM: Unknown Organism
<220> FEATURE:
<223> OTHER INFORMATION: Description of Unknown Organism: Feline
      sequence

<400> SEQUENCE: 34
cagggcaagc cccggcctca ggtgacctgg accaaagagg ggcagccact ggcaggcgag     60
gaggtgagca tccgcaacag ccccacggac accatcctgt tcatccgggc tgctcaccgc    120
gcccactctg gcacctacga ggtgatgctg cggatcgaga acatggagga caaggccacg    180
ctggtcctgc gggtcgtt                                                  198

<210> SEQ ID NO 35
<211> LENGTH: 159
<212> TYPE: DNA
<213> ORGANISM: Unknown Organism
<220> FEATURE:
<223> OTHER INFORMATION: Description of Unknown Organism: Feline
      sequence

<400> SEQUENCE: 35
ggtgcgtggc actggggccc cctctctgag atgcccagag accctgcaga aggtggcagg     60
```

```
ccaggtccag gctggcgggg gtgaggggc ctcccagggc cctctgttca tactccagca      120
gtctcaggag gtctgttccg gctggtctct ctcctgcag                            159

<210> SEQ ID NO 36
<211> LENGTH: 141
<212> TYPE: DNA
<213> ORGANISM: Unknown Organism
<220> FEATURE:
<223> OTHER INFORMATION: Description of Unknown Organism: Feline
      sequence

<400> SEQUENCE: 36
acaagccaag ccctccccag gatattcggg tcactgaggc atggggtttc aatgtggttc      60
tggagtggaa gccaccccag gatgatggta acacagagat cttgggttac acagtacaga    120
aagccgacaa gaagaccatg g                                               141

<210> SEQ ID NO 37
<211> LENGTH: 164
<212> TYPE: DNA
<213> ORGANISM: Unknown Organism
<220> FEATURE:
<223> OTHER INFORMATION: Description of Unknown Organism: Feline
      sequence

<400> SEQUENCE: 37
gagtggttca ccgtcttgga gcattaccgt cgcactcact gtgtcgtctc gggagctcat      60
cattgggcaa cgggctacta cttccgtggt cttcagccat aacacggtgg gacccagtga    120
caacgcggcc accaccaagg agcctgtctt tatccccaga ccag                     164

<210> SEQ ID NO 38
<211> LENGTH: 138
<212> TYPE: DNA
<213> ORGANISM: Unknown Organism
<220> FEATURE:
<223> OTHER INFORMATION: Description of Unknown Organism: Feline
      sequence

<400> SEQUENCE: 38
gtgctgtacc tttactccca cccccgtgct gtacctttac tcccaccccc aggaggagct      60
ggggcaggga ggcggtatga gcagggaggg ggcctagcgt ggtgtggcac tcttggtgca    120
aagtcttatc acccacag                                                  138

<210> SEQ ID NO 39
<211> LENGTH: 139
<212> TYPE: DNA
<213> ORGANISM: Unknown Organism
<220> FEATURE:
<223> OTHER INFORMATION: Description of Unknown Organism: Feline
      sequence
<220> FEATURE:
<221> NAME/KEY: modified_base
<222> LOCATION: (124)
<223> OTHER INFORMATION: a, c, g, t, unknown or other

<400> SEQUENCE: 39
gcatcacata tgagccaccc aactacaagg ccctggactt ctccgagggc ccgagcttca      60
ctcgccctct ggtgaaccgc tcagtcattg ctggctacaa tgctaccctc tgctgtgctg    120
tcgnggggta gccccaagg                                                 139

<210> SEQ ID NO 40
```

<211> LENGTH: 191
<212> TYPE: DNA
<213> ORGANISM: Unknown Organism
<220> FEATURE:
<223> OTHER INFORMATION: Description of Unknown Organism: Feline
      sequence

<400> SEQUENCE: 40
catcccaaga tttcctggtt caagaatggc ctggacctgg gagaagatgc ccgcttccgc     60
atgttcagca agcatggtgt gttcgacctt ggagatcaga aagacctgcc cctttgatgg    120
gggcgtctat gtctgcaggg ccaccaactt acaaggcgag gcacagtgtg agtgccgcct    180
ggaggtgcga g                                                         191

<210> SEQ ID NO 41
<211> LENGTH: 1274
<212> TYPE: PRT
<213> ORGANISM: Homo sapiens

<400> SEQUENCE: 41

Met Pro Glu Pro Gly Lys Lys Pro Val Ser Ala Phe Ser Lys Lys Pro
 1               5                  10                  15

Arg Ser Val Glu Val Ala Ala Gly Ser Pro Ala Val Phe Glu Ala Glu
            20                  25                  30

Thr Glu Arg Ala Gly Val Lys Val Arg Trp Gln Arg Gly Gly Ser Asp
        35                  40                  45

Ile Ser Ala Ser Asn Lys Tyr Gly Leu Ala Thr Glu Gly Thr Arg His
    50                  55                  60

Thr Leu Thr Val Arg Glu Val Gly Pro Ala Asp Gln Gly Ser Tyr Ala
65                  70                  75                  80

Val Ile Ala Gly Ser Ser Lys Val Lys Phe Asp Leu Lys Val Ile Glu
                85                  90                  95

Ala Glu Lys Ala Glu Pro Met Leu Ala Pro Ala Pro Ala Pro Ala Glu
            100                 105                 110

Ala Thr Gly Ala Pro Gly Glu Ala Pro Ala Pro Ala Ala Glu Leu Gly
        115                 120                 125

Glu Ser Ala Pro Ser Pro Lys Gly Ser Ser Ser Ala Ala Leu Asn Gly
    130                 135                 140

Pro Thr Pro Gly Ala Pro Asp Asp Pro Ile Gly Leu Phe Val Met Arg
145                 150                 155                 160

Pro Gln Asp Gly Glu Val Thr Val Gly Gly Ser Ile Thr Phe Ser Ala
                165                 170                 175

Arg Val Ala Gly Ala Ser Leu Leu Lys Pro Pro Val Val Lys Trp Phe
            180                 185                 190

Lys Gly Lys Trp Val Asp Leu Ser Ser Lys Val Gly Gln His Leu Gln
        195                 200                 205

Leu His Asp Ser Tyr Asp Arg Ala Ser Lys Val Tyr Leu Phe Glu Leu
    210                 215                 220

His Ile Thr Asp Ala Gln Pro Ala Phe Thr Gly Ser Tyr Arg Cys Glu
225                 230                 235                 240

Val Ser Thr Lys Asp Lys Phe Asp Cys Ser Asn Phe Asn Leu Thr Val
                245                 250                 255

His Glu Ala Met Gly Thr Gly Asp Leu Asp Leu Leu Ser Ala Phe Arg
            260                 265                 270

Arg Thr Ser Leu Ala Gly Gly Gly Arg Arg Ile Ser Asp Ser His Glu
        275                 280                 285

```
Asp Thr Gly Ile Leu Asp Phe Ser Ser Leu Leu Lys Lys Arg Asp Ser
    290                 295                 300

Phe Arg Thr Pro Arg Asp Ser Lys Leu Glu Ala Pro Ala Glu Glu Asp
305                 310                 315                 320

Val Trp Glu Ile Leu Arg Gln Ala Pro Pro Ser Glu Tyr Glu Arg Ile
                325                 330                 335

Ala Phe Gln Tyr Gly Val Thr Asp Leu Arg Gly Met Leu Lys Arg Leu
                340                 345                 350

Lys Gly Met Arg Arg Asp Glu Lys Lys Ser Thr Ala Phe Gln Lys Lys
            355                 360                 365

Leu Glu Pro Ala Tyr Gln Val Ser Lys Gly His Lys Ile Arg Leu Thr
    370                 375                 380

Val Glu Leu Ala Asp His Asp Ala Glu Val Lys Trp Leu Lys Asn Gly
385                 390                 395                 400

Gln Glu Ile Gln Met Ser Gly Ser Lys Tyr Ile Phe Glu Ser Ile Gly
                405                 410                 415

Ala Lys Arg Thr Leu Thr Ile Ser Gln Cys Ser Leu Ala Asp Asp Ala
                420                 425                 430

Ala Tyr Gln Cys Val Val Gly Gly Glu Lys Cys Ser Thr Glu Leu Phe
            435                 440                 445

Val Lys Glu Pro Pro Val Leu Ile Thr Arg Pro Leu Glu Asp Gln Leu
    450                 455                 460

Val Met Val Gly Gln Arg Val Glu Phe Glu Cys Glu Val Ser Glu Glu
465                 470                 475                 480

Gly Ala Gln Val Lys Trp Leu Lys Asp Gly Val Glu Leu Thr Arg Glu
                485                 490                 495

Glu Thr Phe Lys Tyr Arg Phe Lys Lys Asp Gly Gln Arg His His Leu
                500                 505                 510

Ile Ile Asn Glu Ala Met Leu Glu Asp Ala Gly His Tyr Ala Leu Cys
            515                 520                 525

Thr Ser Gly Gly Gln Ala Leu Ala Glu Leu Ile Val Gln Glu Lys Lys
    530                 535                 540

Leu Glu Val Tyr Gln Ser Ile Ala Asp Leu Met Val Gly Ala Lys Asp
545                 550                 555                 560

Gln Ala Val Phe Lys Cys Glu Val Ser Asp Glu Asn Val Arg Gly Val
                565                 570                 575

Trp Leu Lys Asn Gly Lys Glu Leu Val Pro Asp Ser Arg Ile Lys Val
            580                 585                 590

Ser His Ile Gly Arg Val His Lys Leu Thr Ile Asp Asp Val Thr Pro
    595                 600                 605

Ala Asp Glu Ala Asp Tyr Ser Phe Val Pro Glu Gly Phe Ala Cys Asn
610                 615                 620

Leu Ser Ala Lys Leu His Phe Met Glu Val Lys Ile Asp Phe Val Pro
625                 630                 635                 640

Arg Gln Glu Pro Pro Lys Ile His Leu Asp Cys Pro Gly Arg Ile Pro
                645                 650                 655

Asp Thr Ile Val Val Ala Gly Asn Lys Leu Arg Leu Asp Val Pro
                660                 665                 670

Ile Ser Gly Asp Pro Ala Pro Thr Val Ile Trp Gln Lys Ala Ile Thr
            675                 680                 685

Gln Gly Asn Lys Ala Pro Ala Arg Pro Ala Pro Asp Ala Pro Glu Asp
    690                 695                 700

Thr Gly Asp Ser Asp Glu Trp Val Phe Asp Lys Lys Leu Leu Cys Glu
```

```
                        705                 710                 715                 720
Thr Glu Gly Arg Val Arg Val Glu Thr Thr Lys Asp Arg Ser Ile Phe
                    725                 730                 735
Thr Val Glu Gly Ala Glu Lys Glu Asp Glu Gly Val Tyr Thr Val Thr
                    740                 745                 750
Val Lys Asn Pro Val Gly Glu Asp Gln Val Asn Leu Thr Val Lys Val
                    755                 760                 765
Ile Asp Val Pro Asp Ala Pro Ala Pro Lys Ile Ser Asn Val Gly
            770                 775                 780
Glu Asp Ser Cys Thr Val Gln Trp Glu Pro Pro Ala Tyr Asp Gly Gly
785                 790                 795                 800
Gln Pro Ile Leu Gly Tyr Ile Leu Glu Arg Lys Lys Lys Ser Tyr
                    805                 810                 815
Arg Trp Met Arg Leu Asn Phe Asp Leu Ile Gln Glu Leu Ser His Glu
                    820                 825                 830
Ala Arg Arg Met Ile Glu Gly Val Val Tyr Glu Met Arg Val Tyr Ala
                    835                 840                 845
Val Asn Ala Ile Gly Met Ser Arg Pro Ser Pro Ala Ser Gln Pro Phe
            850                 855                 860
Met Pro Ile Gly Pro Pro Ser Glu Pro Thr His Leu Ala Val Glu Asp
865                 870                 875                 880
Val Ser Asp Thr Thr Val Ser Leu Lys Trp Arg Pro Pro Glu Arg Val
                    885                 890                 895
Gly Ala Gly Gly Leu Asp Gly Tyr Ser Val Glu Tyr Cys Pro Glu Gly
            900                 905                 910
Cys Ser Glu Trp Val Ala Ala Leu Gln Gly Leu Thr Glu His Thr Ser
                    915                 920                 925
Ile Leu Val Lys Asp Leu Pro Thr Gly Ala Arg Leu Leu Phe Arg Val
            930                 935                 940
Arg Ala His Asn Met Ala Gly Pro Gly Ala Pro Val Thr Thr Thr Glu
945                 950                 955                 960
Pro Val Thr Val Gln Glu Ile Leu Gln Arg Pro Arg Leu Gln Leu Pro
                    965                 970                 975
Arg His Leu Arg Gln Thr Ile Gln Lys Lys Val Gly Glu Pro Val Asn
            980                 985                 990
Leu Leu Ile Pro Phe Gln Gly Lys Pro Arg Pro Gln Val Thr Trp Thr
        995                 1000                1005
Lys Glu Gly Gln Pro Leu Ala Gly Glu Glu Val Ser Ile Arg Asn Ser
    1010                1015                1020
Pro Thr Asp Thr Ile Leu Phe Ile Arg Ala Ala Arg Arg Val His Ser
1025                1030                1035                1040
Gly Thr Tyr Gln Val Thr Val Arg Ile Glu Asn Met Glu Asp Lys Ala
                    1045                1050                1055
Thr Leu Val Leu Gln Val Val Asp Lys Pro Ser Pro Pro Gln Asp Leu
            1060                1065                1070
Arg Val Thr Asp Ala Trp Gly Leu Asn Val Ala Leu Glu Trp Lys Pro
        1075                1080                1085
Pro Gln Asp Val Gly Asn Thr Glu Leu Trp Gly Tyr Thr Val Gln Lys
    1090                1095                1100
Ala Asp Lys Lys Thr Met Glu Trp Phe Thr Val Leu Glu His Tyr Arg
1105                1110                1115                1120
Arg Thr His Cys Val Val Pro Glu Leu Ile Ile Gly Asn Gly Tyr Tyr
                    1125                1130                1135
```

-continued

Phe Arg Val Phe Ser Gln Asn Met Val Gly Phe Ser Asp Arg Ala Ala
            1140                1145                1150

Thr Thr Lys Glu Pro Val Phe Ile Pro Arg Pro Gly Ile Thr Tyr Glu
        1155                1160                1165

Pro Pro Asn Tyr Lys Ala Leu Asp Phe Ser Glu Ala Pro Ser Phe Thr
    1170                1175                1180

Gln Pro Leu Val Asn Arg Ser Val Ile Ala Gly Tyr Thr Ala Met Leu
1185                1190                1195                1200

Cys Cys Ala Val Arg Gly Ser Pro Lys Pro Lys Ile Ser Trp Phe Lys
            1205                1210                1215

Asn Gly Leu Asp Leu Gly Glu Asp Ala Arg Phe Arg Met Phe Ser Lys
        1220                1225                1230

Gln Gly Val Leu Thr Leu Glu Ile Arg Lys Pro Cys Pro Phe Asp Gly
    1235                1240                1245

Gly Ile Tyr Val Cys Arg Ala Thr Asn Leu Gln Gly Glu Ala Arg Cys
    1250                1255                1260

Glu Cys Arg Leu Glu Val Arg Val Pro Gln
1265                1270

<210> SEQ ID NO 42
<211> LENGTH: 24066
<212> TYPE: DNA
<213> ORGANISM: Homo sapiens
<220> FEATURE:
<221> NAME/KEY: modified_base
<222> LOCATION: (9517)
<223> OTHER INFORMATION: a, c, g, t, unknown or other
<220> FEATURE:
<221> NAME/KEY: modified_base
<222> LOCATION: (23921)
<223> OTHER INFORMATION: a, c, g, t, unknown or other
<220> FEATURE:
<221> NAME/KEY: modified_base
<222> LOCATION: (23981)
<223> OTHER INFORMATION: a, c, g, t, unknown or other

<400> SEQUENCE: 42

| | | | | | |
|---|---|---|---|---|---|
| acctcactaa | aggacaaarc | tggagctcaa | gtgatctgcc | cgcctcagcc | tcccaaagtg | 60 |
| ctgggattac | aggtgtgagc | cacttcgccc | agcccatttt | tatttttta | ttattattct | 120 |
| ttgagatatt | aataataaaa | aataataata | aataatattt | ttattattat | tatcactctg | 180 |
| tcacccaggc | tgcagtgcag | tggtgcgatt | ttggctcact | gcagcccgga | actccctgga | 240 |
| ctcaagcgat | cctcccacct | cagcctcctg | ggtagctgat | actacaggtc | cacaccacca | 300 |
| cacctggcta | atttgtgtgt | gtgtgtgtat | ttattttatt | ttttattttt | ttagtagaga | 360 |
| tggggttttg | ccatgttgcc | caggctggtc | tcaaactcct | ggcctcaaat | aatctgcctg | 420 |
| cctcggcctc | ccaaagtgct | gggattacag | atgagccacc | acaccggcc | taacattttt | 480 |
| aaaattataa | acccacttca | tacgtgtgac | aatcctgtgc | agtgggtgct | gctttcaccc | 540 |
| acccgctttt | acagatgagg | aaaccaggtg | ctttgagatt | aaagagatgg | cagtgctagg | 600 |
| actcagagac | accctggccc | cagggtctgt | ggacatgacc | actgcctgaa | ctgcctgcga | 660 |
| ggatgctcct | gacccgttag | ccttaggggtt | atgggcccag | catgctccca | ccgtacaatt | 720 |
| tgctgtaaga | gggacacaca | cggggcttgg | agtaccctg | aggcttgcca | aaggttgggg | 780 |
| aggcagaatt | gtgctgcggg | gggtgagggg | gaagggacag | gagccagcca | gggacaatgt | 840 |
| ggccctacct | tctccctgga | gagacctcag | ctctctggaa | ttcatctata | tttagcaggt | 900 |
| ggctggacag | gaggcagata | agcagagcct | ggggaggggg | gaggtcccca | tatatagtgg | 960 |

-continued

```
gaaggacagg accccactca gtccctcttt gggtgacctg tgcctgcttc gtgcctggtg    1020
tgacgtctct caggatgcct gagccgggga agaagccagg tagctttagg actggggttg    1080
ggtctaagtg tgggagcagg ggggtgtcta caattgggga gcagggctag agggagttc    1140 ttgagggggt tgacgaggac gtggcctctg agccccagga caggggcagc cagtcctcca    1200
gggtcctttt ttgattctcg gtttcttttt cccatccctc tgatgagagg tgaaggtaaa    1260
cccaaggtca gggacgcaga gaggggacac agccaagaca ggaagcaccc ggggtcaacc    1320
cattctgaga atgcaaaggg acccttccc tgtcccattg ccttcacctt ccacagcaag    1380
gttccccgcg gacagagccc acgtttagta tggagctgag ccaggctcac ggcatgcctt    1440
cagaccagtc tctacccact atgggtctca gtctcccaac ctgggtgcc ggggtggtg    1500 gtggcattgg gttggttcct cctggctgtg acattatctg cttcatgagc ctgtacggtg    1560
tggcccccat gttgagggtg acacagcccc tcttctctga gagaggacag tcaggagccc    1620
ctgaacccag gccaagggca gggaaaatca gcccagggg acctgggcct gggctgtgcc    1680
cttatgaagg ttgtccaggg cagagatcca ggtccccatc ccccagcgcc ctcccaggcc    1740
agctttatct cagttgctga tacccagcct gaggtccttg gaggacaaat ttggccacat    1800
tccaagtggg cagacttccc cgcccctgc caagggcccg aaatggttgg gggaaaggga    1860
gctgggttca tcacgggtgt ctccaagcag ggaaagtgga cacatgcaga aaaagtcttg    1920
ttgggaggtc aggaccacag ccctggctct cccgactgct agctgtgtga tcttggagga    1980
gccgcttagc ttctctgagc ctcagtgtcc tcctctgaga aatgaacaga ataactgcaa    2040
ctacctcaga gaactggtag agtattacgt gaggggatgc atagaaagtg ctagcacagt    2100
atttactgag aggggctgca ggggcggggt gcacgctcca accaggggcc gctgtagcct    2160
ccacctggcc cttcagtctc agcttttagc aagaagccac ggtcagtgga agtggccgca    2220
ggcagccctg ccgtgttcga ggccgagaca gagcgggcag gagtgaaggt gcgctggcag    2280
cgcggaggca gtgacatcag cgccagcaac aagtacggcc tggccacaga gggcacacgg    2340
catacgctga cagtgcggga agtgggccct gccgaccagg gatcttacgc agtcattgct    2400
ggctcctcca aggtcaagtt cgacctcaag gtcatagagg caggtaagat cctgatcagc    2460
cttccctgag gtttgggctg ctgggggagg ggcagcccag cgactctcca tccatccagg    2520
gaacaggagg tgcttcaca cttcttgcc tttgctgtgg ctgtgccccc cgccaggaac    2580
gccctttccc cctttctgc acatgacctc tctgagtacc cccatgtgcc atcctggctt    2640
gttccagcca tggggtaggt gggagagatg aacaagacac aaccccactc tcccccctgca    2700 gacctccctg gggagatgac cctgcacaga cggccgggaa gccccaggag ctgtggatga    2760
ggggagtgca gcccagtctg agggggctgct ctaaggctgg ggcagagcag ggatggacct    2820
ggagctgttc agggcagatg cagaggacat gggaactgat ggcctgggac ggggaggaga    2880
atgtgagagg caggctggct ctccagctca gcatgagctg cctctgaggg gcccaggcag    2940
cgggaggaca gccatggcag actttcctca tccacagcgg gctcatgggt ccaatgctca    3000
ggagagagag ggtggagggg tctctggtta gtggctgcac cacgactccc atctgatccc    3060
ctccagagaa ggcagagccc atgctggccc ctgcccctgc cctgctgag gccactggag    3120 cccctggaga agccccggcc ccagccgctg agctgggaga aagtgcccca agtcccaaag    3180
gtgagagggg ctgggcaggg aggggcagga tccgtgggta gggcgtgtcc agggcaggtc    3240
tcaaaagcct ttgctgggcc aggtgcggtg gctcaggcct ataatcccca gtactttggg    3300
```

```
aggccgaggt gggcggatca tgaggtcagg agattgagac catcctggct aacatgatga  3360
aaccccatct ctactaaaaa tacaaaaaat tagccgggcg tggtggcggg cacctgcggt  3420
cccagctaac ttgggaggct gaggcaggag aatggtgtga acctgggagg cggagcttgc  3480
agtgagccga gattgtgcct ctgcactcca gcctgggtga cagagcaaga ctccatctca  3540
aacaaacaga aaaagccttt gctcacaggg tcaagctcag cagctctcaa tggtcctacc  3600
cctggagccc ccgatgaccc cattggcctc ttcgtgatgc ggccacagga tggcgaggtg  3660
accgtgggtg agtgtgagct gctgtgccca gcattgggt gggaagggg ggcagcagga  3720
cactccccaa gccgggcctg tcgccctgcc tttgcaggtg gcagcatcac cttctcagcc  3780
cgcgtggccg gcgccagcct cctgaagccg cctgtggtca gtggttcaa gggcaaatgg  3840
gtggacctga gcagcaaggt gggccagcac ctgcagctgc acgacagcta cgaccgcgcc  3900
agcaaggtgg gtccaccggg gtcgtggaga cacggagaga ggggacatgg agagccctag  3960
aaggcacaag gcacacagag ggcaccatga gacccagagg cacacacgag ctgcaagcaa  4020
ggggtgtggg gaatctggga ggcaggtgga ggggccaggg gcccacaggg agatcccgga  4080
ggcctggggg ccagggagtg cgatgaggct catgggagca ctgtcgggga cctgggagac  4140
ttggtggaca tgatcaccctc aaggggcac ctaataaggt ttggccgggg gtgggggggc  4200
gcccagggtg gtcaggaagc ctggaggaca ctgtgaagca tgggggcacc agctagtggg  4260
gttgtaaagc cccgggatgg gtgagtatca gggctaaggg ctcaagggac tctcagggat  4320
taaccagaac aattcctcat tatacagaca cggaaaccaa agcttgagag gttaagtggc  4380
tgctccaagg tcacttagac ataggcctag aaccttaagc cttcgttttt tgtgttttgt  4440
ttttttccgc cctgcccacc agaaccttaa ggcttaagtc cccttgtttg ttcactccaa  4500
gcctctgctt ttcccaacct tccccagtcc tgggctaggc aaggggggcct ctagcaagag  4560
aggccaacat gttctgctgt gcggggctgt gcattgcaca aaagcctgta tttcaccaca  4620
accgtgtgcc agcagatggc aatcatgggt ttcgagatag tcccctttct ctgtacaaaa  4680
actctgtatg ggttaactaa agcctgaggg tgcgaagatc gatgagcatt tgtcactccc  4740
agcctccttt aaatatatat atatatatat aatttgagac agggtctcgc tctgtcgctc  4800
aggctggagt gcagtggctc aatctcggct cactgcaacc tccacctcct gggttcaagc  4860
gattctccca cctcagcctc ccgagtagct gaaactagag gtgtgcacca ccatacttgg  4920
ctaattttcg ttattttag tagagacgga atttcaccac gttggccagg ctggtctgga  4980
gctcctggtc ttatgtgatc cgcccgcctc agcctcccaa agtggggatt acaggcctga  5040
gccaccgcgc ccggccactc ccagtctcct ttaagggtgc ggagccttgt ctcccggccc  5100
ctggtgtccc ctgacgcccc gtccctccat gcacacaggt ctatctgttc gagctgcaca  5160
tcaccgatgc ccagcctgcc ttcactggca gctaccgctg tgaggtgtcc accaaggaca  5220
aatttgactg ctccaacttc aatctcactg tccacgtga gggggccctg tgtctgtcc  5280
tgggctcggg ctccccatgg gtcctggtct cctacctcct tttcccaaca ctaaggagga  5340
tgcctcgtcc catccagaca tgagtgctgg ccacgtgccc agtgctgcac acacagggtg  5400
tgagagaaac cccaaggctt gcagggtagg cgtgggggct tagggctgag tccgggtctc  5460
atctgggtgg gactctgttt tatcatcttg gtgtcacggc tcctggccca cggcctggca  5520
ctgtctgaat gttggggcga tgggtgaagg tgagttgaga gatgggtggg aattggggac  5580
aataaaccgt cccacctgcc tggtacccttg accctgggaa aggctgggaa ggtgagatcc  5640
tggggcagat gcccagcctc atgggtcat gaatgggcaa gtctgtgaat actcagaggc  5700
```

```
cgcccccagg gcagggcttc tcaaacggcc ccctctgaag cccccttcccc catctctcca    5760 ccctttgaac ccagaggcca tgggcaccgg agacctggac ctcctatcag ccttccgccg    5820
cacgtgagtg gccatcctca gggcctgggg gaggccagtg ctggagtctg aggcccttca    5880
gggtctcgac tgggggtcag ggctggggat gatttgcggg gcggagctga agtcagtggg    5940
ggctgcaggg gagagcaagc ttcccaggca ggtgaggata ctgagtctaa cccccacagg    6000
agcctggctg gaggtggtcg gcggatcagg taccccctgcc ccaggcccta cctgcaccat    6060
ccgcagaccc ccaggggtct gagacgggtg ggagcccaat ctggctagtg tcccttctctc   6120 cctccccact ccactcccat cctgctccta atccctttcc agtccctcac tgcagcctca    6180 ctggggtcc ctctccatag tgatagccat gaggacactg ggattctgga cttcagctca    6240
ctgctgaaaa agaggtgagt cctgggtggc agttcctggg gcagctggtg aggcctggct    6300
ccaaatccca gcactgtggt ttgccagctg tgtgaccctg agcacaacac tgcacctctc    6360
tgagttggtt tccttgtctg tcgaggggat gatcccagtg tggaaggagt taaagggctc    6420
tgcagacatt atgtcccgtc aacagtcatc ctcacagtgt cccccacggc cactccacac    6480
ttgaggctgc aaaagctccc tccgtaaact ccggggaccc agaaggaaca gagagagggt    6540
ccccagagct gcagggtcta ccaggtcggc ccaactgact tatgttctct ctgccctctc    6600
tctccctctc ccccggcccc tccattatgg ctgctgctgc tgtggcccag agagtaagaa    6660
tcggggtctg ggtgtttggg ggcggcaggg cgctggtggg tgcagagggg attcccgtcc    6720
cctctctgag aggctgtggt gagagactca gagcagggtg cggctcccca cggacagggg    6780
tgagtctctg tgccttgggc ttctcctgcc acccacctat ctgtcagagc ttaggaggga    6840
taagaaaaag taatgcacac aggaggtcct gccagagcct ccggagcagc atgggtgccc    6900
cacaacacag ggagtgcaag tgcggaaaat agggaggaag taaaggccca tgggtggggt    6960
ccaggtcttt gagggaaggt ggccatacct ctcatgtgcc acctaccctt tctcccaccc    7020 ccaccctgg agcagcagtt tccggacccc gaggtgagtg cccaacatag cacagcaccc    7080
tcatcacccc taattctgcc aggagcccct ccagatcccc agcccctctt cagctcccctt   7140 ggccccagt cctgcctggc ctgggaccca gagcagctcc agctgcccca ccagaaggga    7200
aggggcagag ggacagggt ggctacagct ccttggtcct gggcccagga agccccgccc    7260 aggggctgc agtcttgccc ccggccacag cctagactgc gggacacagg gactcgaagc    7320
tggaggcacc agcagaggag gacgtgtggg agatcctacg gcaggcaccc ccatctgagt    7380
acgagcgcat cgccttccag tacggcgtca ctgacctgcg cggcatgcta aagaggctca    7440
agggcatgag gcgcgatgag aagaagagca caggttagcc cttcctcaga ggggagagga    7500
gagggcacag gctagcccctt ccctacacag gagaggagag ggcataggtt agcccttccc    7560
cacagggaga ggagagggca caggttagcc ccccacctcg tccacataca tggaaagagc    7620
ggagtccggc ttagcacaga gactcacagg aaagaagagc ccaggttaac ccctccttgt    7680
gtagaaaaag ccaagaatgc ccaggttagc cccttaccac agagatagaa gagaagagca    7740
aaagttaggc caggacagcc acaaggaaaa ggacagagct caggttaacc ctcctcacca    7800
aggaaaaatc aggctacact ttctttctct accctcttct gaaagaaat gaagcccggt    7860 taaccctctc cacacccaaa agaaaaggga agaggcccgc taagcctgga gagccacaca    7920
caggcaaaga aaagagcctg gctaatcttt ctctcaggca aacaaagcag gagggcttgg    7980
gttaactacc ctcacccccca ggcagatgga aagaggagag cccaggaata gcccttctcc    8040
```

```
actgaggggt tgacaagggc gggtgtgagc cgggaaagca ggggtctcac atgccttctc   8100
cccaccatgt ctgggtctag cacagggcct ggcacacacc tcgagcgctc tataaacacc   8160
gactgaatgg aggggtcagc ttccatgcag gatatgggag acaagcccct cccaaagcac   8220
acacacaaaa cacacacgat catggggacg gggagaggag ctggttagtc cctccctgct   8280
gacctccccc aggcccctta tccctctgcc ctgcctccct gttgtctcag cctcactggg   8340
tttcccatca ccccatcgct aggtggcctg gcccttaccg gcaccgtggc cccatttaag   8400
ccagggatcc cctgaatgcc accaatgttc ctctgggtta actcctgaac tgctgagccc   8460
agagggcacc aagcaaagga ctgtaggtgc caaggagga aaagatggag ctggcaagg    8520
cagatgggga cctccgaggg taggggtgtc ttccaggaat agcaacaaca gtaaaaagag   8580
caaattgctg gccaggtgca gtggctcacg cctgtaatcc cagcactttg ggaggccgag   8640
gcaggtggat cacctgaggt taggcgttca agaccagcct gaccaacatg gtgaaacccc   8700
gtctctacta aaaatacaaa attacctggg catggtggca ggcgcctgta atcccagcta   8760
ctccggaggc tgaggcagga gaatcacttg aacccgggag gcagaggttg cagtgagtca   8820
ggattgtgcc attgcactcc aacctgggtg acagaatgag actccatctc aaaaaaagtg   8880
agtgagtwgc cttcctaagc cagccactag gtgctttatg taattatctc atttaattct   8940
cgaaacaaca ctatgatgga aggactatta ccatttccat gttactgagg aaaccgaggc   9000
acagagggtt taaggaacta cgcaaggtc acagagcacc cagcagtaga tctctgcccc   9060
tccgcagctg actccaggcc cagccagagt atttgaggac tcaggggtcc ttctctgctc   9120
ggtggatgga gcccccactt cctccctggg ctcagcagca gcaacatggg cttttacaaa   9180
cacggccgca agaggaggca ttgttgtgga gcagggctgg gctcaagacc cagctctgcc   9240
acacacctgc tgggctggtg gcattgggcc agtcgcctct ctgagcccta ttccccactg   9300
cagcagcatg gggacacgca ctggcctggg ggctgagatg gagtgagwgw gactskgcac   9360
agaggctgct agtggagcgc ctggcagagt acacactcag ggttgytgag agagagaggc   9420
acagctgtcc agcccagtct ctgacagcts ygtcttctgg agccctaacc catccttgag   9480
tgagcagtga gagaccccaa ggagacagag gacaagntct gacagacaga gaccaggagg   9540
tgggttgaca cctgacacga taaagaaatg aagacaccat gcctgtaatc ccagcacttt   9600
gggaggctga ggcgggcgca tcacctgagg tcaggatttc aagaccagcc cggccaacat   9660
ggtaaaaccc cgtctctact aaaaatacaa aaattagctg ggcgtggtgg cacatgcctg   9720
taatcccagc tactcgggag gccgaggcag gagaatcact tgaacctggg aggcagaggt   9780
tgcagtgagc caagatggcg ccattgcact ccagcctggc caacagagca agactctgtc   9840
caaaaaacaa acaaacagac aaacaaacaa aacaaaaaga aatagagaca cagagaagtg   9900
gaagcggggc ggcacagagg ggattggagg gggggacctg gccccagcc acagccacag    9960
tagcttggcc tggggagca gggtgcgggc ggtggggtgg tcgggctga ggggtggtgc    10020
tcagcctttc agaagaagct ggagccggcc taccaggtga gcaaaggcca caagatccgg   10080
ctgaccgtgg aactggctga ccatgacgct gaggtcaaat ggctcaagaa tggccaggag   10140
atccagatga gcggcaggtg cagcctgggg tggggagggg ggctcgggtg gaggtgggga   10200
cccccatagc cttgcctcct gccctctccc acatgcgtat ctctgactcg gtgtggctct   10260
cagccccatc tctctgggcc taatttccca tccttttgct cctgccggtc cctctctctc   10320
tctccttttg tctcgggctc acttcctccc gtcgggaaca cttcaacggc cccttctgtt   10380
ctacagcaag taagttcccc tctggatggc ttggggtggg gggcacaggg attatcacgg   10440
```

```
ggcgcactgg gcccggaggg gtgtccgcag ctttcctgcc acttccctgc ggcccccacc    10500
caggtacatc tttgagtcca tcggtgccaa gcgtaccctg accatcagcc agtgctcatt    10560
ggcggacgac gcagcctacc agtgcgtggt gggtggcgag aagtgtagca cggagctctt    10620
tgtgaaaggt gggcctggga cctgaggatg tgggaacctg ggaggagat ggcctcaggg     10680
gagccaaccc tcatgctcac cctgcctgga cagagcccc tgtgctcatc acgcgcccct    10740
tggaggacca gctggtgatg gtggggcagc gggtggagtt tgagtgtgaa gtatcggagg    10800
agggggcgca agtcaaatgg tgagttccag aagcacgggg catgggtgtt ggggcatct    10860
gcccagaaga ggccacagca cttgccaccc acccacccgg ctaggctgaa ggacggggtg    10920
gagctgaccc gggaggagac cttcaaatac cggttcaaga aggacgggca gagacaccac    10980
ctgatcatca acgaggccat gctggaggac gcggggcact atgcactgtg cactagcggg    11040
ggccaggcgc tggctgagct cattgtgcag ggtgagcctg gctgggggg cacatgaggc     11100
tttagggctt ggacccctca gccccaccc cacctagccc tgtagggag caggcaaacc      11160
tgggctcaag gcctctgtga ccttgggcct ttgacagcct aaacctcatc cttctcatct    11220
ctaaaatgac gatgctgagg tgaccgctcc agagggtact gagagggtca tacgggcctg    11280
gtgagcatca ccaccctca gacacttgag gttccttatg tgcactgcac catcacaggc     11340
aaacatggca cacacaggca cacgtgtttt cacatgccca catgcaccca gacacgtgcg    11400
caccagcgcc catgggccca cacgccctcc acagggattc acgccacacc cacacaccct    11460
cccgagctca atggctctgc cctgcccgc agaaaagaag ctggaggtgt accagagcat     11520
cgcagacctg atggtgggcg caaaggacca ggcggtgttc aaatgtgagg tctcagatga    11580
gaatgttcgg ggtgtgtggc tgaagaatgg gaaggagctg gtgcccgaca gccgcataaa    11640
ggtgtcccac atcgggcggt gagtgtgcag ggcaggtgga tgggacaggt ggagactgag    11700
atggagacag agagagacac agggagaaac agagagagag agataaagac aggtggacag    11760
agaggcagat gcacagagac aggacagaga ctgagacaga gacccacaga gagggagaaa    11820
cagacagacc caaaaagaca aagagacaga aagacagaaa tagttctata gagacagaaa    11880
gatatgcaca ggggaggcac acacatagga gagttcgtca gagacagaga agaacagagg    11940
gacagagaca aagaggcagc agggagagac acggacgggg tcgagagctc cccagcaccc    12000
tcccccagct tgtgaccagg gcagggcagg aggccaccaa ggaggccggc tctggccaga    12060
ggccctcact gcctctcccg ccctcttgct catccctgga gcaactgggc tggccgtgct    12120
gggcccaagt tcacagagat taatgagacc cagcccctgc ccagtctcca agggcccagc    12180
caaggagatg ctttgatgta gaaatcactt ttacgctgcc tacctctgaa ggcacattaa    12240
aaagctggaa aattagataa tatagaaaaa aaaaggcatt tttaaaaatc agaataccaa    12300
caagccagga caaggtgagg gcctcctggg accctggctg gggtatctgg caaggccagg    12360
ggtgtgtggc ccagtggggt cccctgagcc actgctcccc tgcagggtcc acaaactgac    12420
cattgacgac gtcacacctg ccgacgaggc tgactacagc tttgtgcccg agggcttcgc    12480
ctgcaacctg tcagccaagc tccacttcat gggtgagcct gctccaggt agggtgggtc     12540
ggggcagtgg ggccaggagc ccctgtcact gggccctgcc tttgccccg tgctacttgc     12600
tcttccttct cttgcagagg tcaagattga cttcgtaccc aggcagggta agtcttgggg    12660
cccctgagtc ttggttctgc tcactttccc gcaacccacc cacgcaggcc tcccctccac    12720
tcacagaggg aagagcaagg atcaaaagtg ggggtcctgg ggcccagctc cagctttgcc    12780
```

```
actcatgacc atgggtcaat tataatctct gtgagcctca gtttcctctt ctctaaaatg   12840
ggaaccctga tagtgccacc tcataggata gttataaaga tgaggtgaca tgatgtatca   12900
gacctgtcaa gtgctgtcac acgtgtgact gttattatta catcttttct tcttcttcct   12960
ttttttttat ttttattttt tttgagacgg agtctccctc tgtcgccac gctggagaga    13020
agtggcgcga tctcggctca ctgcaagctc cgcctccag gttcacacca ctctcctgcc    13080
tcagcctcct gagtagctgg gactacaggc gcccgccacc atgcccagct aattattttt   13140
tgtattttta gtagagacgg ggtttcacca tgttagccag gatggtttcg atctcctgat   13200
ctcatgatct gcctgcctcg gcctcccaaa gtgctgggat tacaggcgtg agccactgcg   13260
tccagactgc tttgctttgt ttaactgagg gcagattcct gatttatttg gccagggaac   13320
ctttttaatg tgtgcatgtg tgcgtgcatg tgtgcgcgcg tgcgtgtgtg tgcatgtgtc   13380
tgtgtgtgta tgtatatatg tgtgtctgtg tctgtgtgtg tgcgtgtatg tatgtgtatt   13440
tgtgtctgtg tgcatgtgtg tgtctgtgtg tgcatgtgtg tatgtgtatg tgtgtctgtg   13500
tgtatgtgta tatgcgtgtg tgtgtgtgta ttgtgtgtgt gtgtatgtgt gtggcaagac   13560
actgatgttc ccccagtttt caaaatgcta tgctaggtga cctgacctga atattacaag   13620
cctcccagcc aacgtcctgg ggtgatggga atgttccaga tcttggttgg attaataatt   13680
gcatgggtgt attcatctgt cagaactcag cctactgtca gatctgagca taaactatac   13740
ctcaatacaa atctaaaaaa ccaataacca ggggcccagg ctcttgagca gccccgcccc   13800
agtgacctgt gctcctcctg gctctcccgt ttctctgaac tacattgtgt cttctgcaga   13860
acctcccaag atccacctgg actgcccagg ccgcatacca gacaccattg tggttgtagc   13920
tggaaataag ctacgtctgg acgtccctat ctctggggac cctgctccca ctgtgatctg   13980
gcagaaggct atcacgcagg tactgtgggt ccctcctcag tctccccatc tataagatgg   14040
gtgtgtggaa ccagccaagt gctaggacct gctgcacacc ccacccacat gtgcacgccc   14100
tgctgttggc taccccgtgg gagagactgg tcaggggca ggcaaggtgg gcagtgtggg    14160
tcaggggtg gaagaagcag cagagggcg cttccaggct gagtcagctc ctctgctccc     14220
tacttccctc ctgccctgtt cccaggggaa taaggcccca gccaggccag ccccagatgc   14280
cccagaggac acaggtgaca gcgatgagtg ggtgtttgac aagaaggtga gtgagactga   14340
ggtcaggagg aggctcgttt gtctttcatc actttctacc tacgtggtgc cgagcccttg   14400
gcgaggtctc catggaggtg ccacacttgg ccgggtgtgt tgctgccccc agcagggtcc   14460
ctgtggggcc ctcacacctc aggcagaggg tctctgtgaa gtgtgctgat ggccatcaca   14520
aggatgtgga caccctctca ttgccaggaa gccctcatga ctgggctgct ccctggctcc   14580
cttcatccta agctgacctt gaccttgacc ttgtgctccc tctcaactca ggagtagttt   14640
ctgagacact tttctgccag tgtagctgcc ggggtcttgc tcctgcctgg cactgttggt   14700
tcttctgaag gctggggtct tgaggggtcc tcatgatagc tcatctgaga ggacaggtgg   14760
ttgccccagg tcccgtgaca aagctagaac ccgagcccct gccctcagtc ggtgccacag   14820
agatgatttt gaactagatg ctgacgtgga tgcagtcttc ccacaggctg tgttcccccc   14880
atggaccccc gggacatctg gctgttggcg gaggctgcaa gggcctctgg ggtctgactt   14940
ggatctcacc ccaactctgc accccccag ctgctgtgtg agaccgaggg ccgggtccgc    15000
gtggagacca ccaaggaccg cagcatcttc acggtcgagg gggcagagaa ggaagatgag   15060
ggcgtctaca cggtcacagt gaagaaccct gtgggcgagg accaggtcaa cctcacagtc   15120
aaggtcatcg gtgaggccgg ccggggtcca agctggagaa cacagagggg cagccccaag   15180
```

```
gagggcccat ccgttcgctc attcagccac tcgacaaaca tcacgggcat gctccctgag    15240
ccgagcggca acaggacagg tttttctgcc caaaaggagc cccgctctgg gggagatgga    15300
ggcagatgca tccagcagat ttcctgcgac actgctgtac atgagccatg tccagagtgc    15360
cgtgggagca ctgagcagag agccatccct gtgcctgggg gtgatgcctt taggaggctg    15420
agaagatggt gaggaaaggc atcccaggca gaggaaactg tgtacaaagg ggtggaggag    15480
ggaaagggcc ttttgggtgt ggagaatgaa tgaaacatgt caggagagga ctgggtgggg    15540
ttgggaggat cagagccagg acaggggtga atatgggcag tgagaagcct taaagggttg    15600
acggagggct ggcgacatga tcagaaatgc atcctgttga ccccagcct ggacaacaca    15660 gtgagactcc atatcactaa aaaaaaaaaa aaaaaagga aaagaagaaa gaaatgcatt    15720
ctagaaagat ctctttggat ctgggggtgg tgggggcagc ctgtggcggt tagttggagt    15780
gggaagggga cgagcaacgt tactcaaggc ctgagcgggg cagggctgat gtgggtccat    15840
cccaccccat ccagacgtgc cagacgcacc tgcggccccc aagatcagca acgtgggaga    15900
ggactcctgc acagtacagt gggagccgcc tgcctacgat ggcgggcagc ccatcctggg    15960
tgagtgcaag ggcaccggat ggaggtgtga gggcgccaaa cagatccgag ggaaggtggt    16020
gtggggatgc ctgggttcca gaccagagct gccacctccc ctgagccagg ctacatcctg    16080
gagcgcaaga agaagaagag ctaccggtgg atgcggctga acttcgacct gattcaggag    16140
ctgagtcatg aagcgcggcg catgatcgag ggcgtggtgt acgagatgcg cgtctacgcg    16200
gtcaacgcca tcggcatgtc caggcccagc cctgcctccc agcccttcat gcctatcggt    16260
gagcctgcct ggcctggtcc tgccccccgc ccctcccca gttaaaaacc tccaataata    16320
gcaggtgctc tgcaggcagc catgctagac actcacatcc acagtctcct ttcatcctcg    16380
actggggata tcagccgca ttttacagat gaggaaacag gctccaagca gttaaatgac    16440
ctgcttgaga tctcccagct ggttggggtg gagctgactc tcacactacg ccgaccccta    16500
gttcacgttt caagcctctc tttccatgtc tacaaaatgg gaataatgac actgcctatc    16560
tcagagagct gttaggatga tatgggatga ccaggcaggc catctggcat ctaacaggtg    16620
ctcaataaat gttcattgtc ccctgttctc cacacccttc aacccagggt tttcacctat    16680
gggatggggc aagggctgta gttagtggag gggtctcagg ggcatctgtc tgtggaaaga    16740
gtcctggacc aagactcaga gatggcagag gcagctccat ggtccccggg gggccaactg    16800
gagtcatccc tccctgaagc ctcagcttcc tcatctgtat aatgggggtct gagtgggcag    16860 aacaggtgtt gagactgtgg cagggctcag gaggacacct gttcccacta gggtgggtga    16920 gtccggggc agctgcctgt ggcaagggca ggccaaggac ccctgggccc agggatgggg    16980
cacagcttgg gaagatggca ggaatcgggg cctgtgggga aagggtcca ggcctctcgt    17040 tttagggact gattcctggt ttgttcagtt cttagtcaac tcacctaatc atacgtgcca    17100
ggaaattccc atgttttctg tagttttagt tttagttttt ttttttttt ttttttttg    17160 agatggagtc tcgctctgtc acccagactg gagtgcagtc ctggcgcgat ctggggtcac    17220
tgtaaccttc acctcccagg ttcaagcaat tctcccacct cagccttctg agtagctggg    17280
attacaggca tccaccacca tgcccagcta attttgtat ttttgtagag acggagtttc    17340
accatgttgg ccaggctggt cttgaactcc tgacctcagg tgatcctccc acctcggcct    17400
cccaaagtgc tgggattaca ggcgtgagcc accgtgcctg gctgctgttg ctgtttgttt    17460
ttaagccaat ctacagacat gtcttgtaac agggacaaaa tattccttaa agtggccaaa    17520
```

```
agccagctga acaggaagtg cccctatgt gaccagtggg cagttcagag tctagggcat   17580
ggatctccag cttccccagg cttgctcaga cccctctctg acctctcctc tgcccaggtc   17640
cccccagcga acccacccac ctggcagtag aggacgtctc tgacaccacg gtctccctca   17700
agtggcggcc cccagagcgc gtgggagcag gaggcctgga tggctacagc gtggagtact   17760
gcccagaggg ctgtgagtgt ccccgccccc aaccccctc cccaaaggaa gaacatgctc   17820
accttgccat tgagcagatt cacctgtagt caagtttttt aggcccactt ttgccgaaag   17880
ttgaggacac ccagagaaat atctgtcctg ttttcagaag taaaaaagct tgcctagtga   17940
aaaacaaatg cagagtaaag ctgactgtaa cacttctttg agcagtgcga aatcagcaac   18000
tacattttaa aaacatattt aaggccaggt gcgatggctt acgcctgtaa tcccagcact   18060 tgggaggcc aaggtgggcg gatcacctga ggtcgggagt cgagaccag tctgaccaac   18120 gtggagaaac cccgtctcta ctaaaaatac aaaattagcc gggtgtggtg gtgggcacct   18180
gtgatcccag ctacgcggga ggctgaggca ggagaatcac ttgaactcgg gaggcagaag   18240
ttgcggtgag ccaagatcat gccattgcac tccagcctgg gagacaagag cgaaactcca   18300
tctcaaaaat aaataaacaa ataaaaattt aaaaaaacat atttaaatcc tggagattcc   18360
tatcagagga gtgggcagtg ggagtggggt gtcagtggtg acacagcctg tggccttgcc   18420 tcccctccc caccccagg ctcagagtgg gtggctgccc tgcagggct gacagagcac   18480 acatcgatac tggtgaagga cctgcccacg ggggcccggc tgcttttccg agtgcgggca   18540
cacaatatgg cagggcctgg agcccctgtt accaccacgg agccggtgac agtgcaggag   18600
atcctgcgtg agtgccccctt tgtgcagtca caagacccgc cattgacacc ccaggccctt   18660
ggtgtccagt ggaggtgggg acagttgggg aggcccagaa tgctctgccc agaacgctgg   18720
gcagagacag gaggggttgg agccatcgtc catgcgctag gcctagggaa aaagtgcaga   18780
gagggtggcc aggcacagtg gctcaagcct gtaatcccag cactttagga ggccaaggca   18840
ggcagatcac ttgaggtcag gagtttgaga ccagcctggc caacatagtg aaaccctgtc   18900
tctactaaaa atacaaaaac tagccaggtg tggtggcgcg tgcctgtagt ccctcaacta   18960
cttgggaggc tgaggcagaa gaatcgcttg gacccgggag gtggcagttg caatgagctg   19020
agatcacact attgcactcc agtctgggtg acagagtgag acaacgtctc aaaaaaaaaa   19080
aagtgcagaa agggctctct tggtgtatgt cagtcccta gttctggaac agggaaagta   19140
aaagccacag tacccaagct ctcttccagg agtgtctcag ctccaacagg taaatattgt   19200
ctatgtagtc agattggtcc ctctgggatc cacttcccat tcctttgttc cttgtcccaa   19260
caaagggtcc atcttttgta aggattggtt ctcaaagctg gaacgaggca gcaaactcag   19320
gtggtaacaa cacagggcat agggtgtcaa agcccaggct tacaccctgg tctatgactt   19380
actagctgtg tgacttcagt caagttgctt accctctctg atccctgcct tttgaagtgg   19440
tgaggctcgg ggaagccagc tgggcttggg cagcctggag ttgctgtgtt agcaggagct   19500
aaaggaggcg cagggcccag caggcagctt ttttcttagc tgcagctctc tgggccttgt   19560
ctcaagggag gttggagctg tggagcccct cagagctgtg gcgggccctc acttagctac   19620
ccactctata cccacagaac ggccacggct tcagctgccc aggcacctgc gccagaccat   19680
tcagaagaag gtcggggagc ctgtgaacct tctcatccct ttccaggtgg gactggcccc   19740
cttccctgtc ccccagggga gagaggctat agtgtgttgt tcccatccag tggactgatg   19800
tctcagggct ggcctgatct gaggtaccag aggctgggt ggcggccggc ccttggagtg   19860
atccaggttc agggttaagc ttttcctccc ctcagggcaa gccccggcct caggtgacct   19920
```

-continued

```
ggaccaaaga ggggcagccc ctggcaggcg aggaggtgag catccgcaac agccccacag    19980
acaccatcct gttcatccgg gccgctcgcc gcgtgcattc aggcacttac caggtgacgg    20040
tgcgcattga aacatggag gacaaggcca cgctggtgct gcaggttgtt ggtgcgtggc     20100
caaggcctcc ttgagccccc ttgtttccct tccctgggct gggctgctgg ggccaagggt    20160
ggggccaggg gacccaaccc acagctcaca ttttccagtc cactgcccca gcaggcctgg    20220
ccctggttgg caggggtggg gtggtccctg gagccagtga ccccctgctc actgtcagga    20280
ggcgtggtga cccaactggg tctgtctccc gcagacaagc caagtcctcc ccaggatctc    20340
cgggtgactg acgcctgggg tcttaatgtg gctctggagt ggaagccacc ccaggatgtc    20400
ggcaacacgg agctctgggg gtacacagtg cagaaagccg acaagaagac catggtgagc    20460
ccagggtctg gggtccccac gtgcaccctg cctaggcccg gcagacccag gccgcagcta    20520
cccttcactg tcctcaccgt ggaccccctca ccctccctct gctgatctga atccctccat    20580
agtaggggtg gagatgccaa gggcacccag gagaggctct cggcatcagg aagggcctgg    20640
cccagagatg cctcccctcc ctccctgccc ccaggagtgg ttcaccgtct tggagcatta    20700
ccgccgcacc cactgcgtgg tgccagagct catcattggc aatggctact acttccgcgt    20760
cttcagccag aatatggttg gctttagtga cagagcggcc accaccaagg agcccgtctt    20820
tatccccaga ccaggtgctg taccctcatt cttccaacca ggggctgggg cagggaggct    20880
gtgggaacag ggagaggggc ctagctttgt gtggcctctc ggtaccaagt cctgtcacca    20940
acaggcatca cctatgagcc acccaactat aaggccctgg acttctccga ggccccaagc    21000
ttcacccagc ccctggtgaa ccgctcggtc atcgcgggct acactgctat gctctgctgt    21060
gctgtccggg gtagccccaa ggtagggaac tttaggcgct ggtccaggcc gaccaggagg    21120
cagggctcac aggccccgac gttgagcagt cctctcccca gcctgtctcc cctgctttct    21180
ctccaccttg gggtgtatgg accgggttcc tccccctggg cagggccatg gtactcactc    21240
ttggttccat gtttgtttcc agccttgggc atagtcaggg actctcgtgg gacccccga    21300 gtagaaacac agatgtgtct ccctgggtcc ctgccaggtc ccctctcagc ctggatggct    21360
tccctccctc tctttacctt atttatagcc caagatttcc tggttcaaga atggcctgga    21420
cctgggagaa gacgcccgct tccgcatgtt cagcaagcag ggagtgttga ctctggagat    21480
tagaaagccc tgccccttg acggggcat ctatgtctgc agggccacca acttacaggg      21540
cgaggcacgg tgtgagtgcc gcctggaggt gcgaggtgag gagccctcgg ggccagggcc    21600
tgggagatgg gaagagcggg cggcagtggg gaccctgggc tttgctccgt tgtcctcggc    21660
caagcacctg ccctggctgc aagggcacgg accctgccac gcccagatgg gcaatagctt    21720
ccagaaggct gggaggacac agtgacatgg cctcctcttc tgcagtgcct cagtgaccag    21780
gctggctcct ggggatggcc aggtatgtac cacccgacac ccagggcaca agtcagtggc    21840
tgagccctgg cccttggtcc tggggcagcc atcagtaaat gggaggctgt aggggccctc    21900
cattcactcg taagataacc tgtgttgcag gtacaaccgg atgccagccc cgtgccagga    21960
gcctggaggg aagttgggga aaccctccc tactgttgga tgtatgtgtg acaagtgtgt     22020
ctcctgtgct gcgatggggg atcagcaggg cagttgtcgg gcagtcctga gtgggtgttg    22080
cacagactgg tccacagggc tcctgaagga agccctggga tctttggggt aaaaggaggg    22140
tggcctcaag aaacaatgtc tggggacagg cctttctggc ctgctatgtc ttcccaatgt    22200
ttattgggca ataaaagata agtgcagtca cagagaactc actcttctca atttcggtgt    22260
```

```
gcctgttttc ataaaaatgc acagggatg gccaggtgcg gtggctcatg cctgttatcc    22320
cagcactttg ggaggcggag gcgggccgat cacctgaggt caggagatca agaccagcct    22380
ggccaacatg gtgaaacccc gtctctacta aaaatacaaa aattagctgg gcaaggtggc    22440
gcgcctataa tcccagctat ttggaaggct gaggcaggag aatcacctga acccaggagg    22500
tagagtttga ggtgggccga gatcatgcca ctgcacttca gcctgggtga tggagtgaga    22560
ccatgtctca aaaaaaaaa aagaaaaaac cccagggaca ttgatcttca cagcaaagtg     22620
agagcagata ctgttttttg ttttgttttc ccgatgatta aaccaggccc agagtggttt    22680
ctgagttcat aaaacattaa cgctagaagg aacctgtctt cccctacagc attcactctt    22740
cagatgatga aactgagctg tgacagcgga aagtgcattt aactggtccc aggtgctcag    22800
cgtgatcctt gtgccagggg ccgtggtcac aaccgcctgg aggtggggtg aggcagaatc    22860
tcagtgttgt gattgtgctg gggtggagct gcactaggtg gctttggagt cccagccagc    22920
aataagccag cagcgggttc agacccatat ccccggtggg agacagcaac ccaatccagt    22980
ccaggacgct gggcaccaga aaggtgtcag ggccagggcc ccactctgct ctcacttccc    23040
ccatggggag cctaaatccg agcatctgtt tcctttgg gcgcgggaagc cagcaggtct     23100
caaattccct gagagtgcag ccaggttttt ccaggacaga attccatgaa ggcagctcct    23160
aggggagctt ctgggagttc tatgcagtgg aagacactcc tggccaggag tccggggccc    23220
tgtgggaggc cctggctgaa tcaccacacc tctctcgacc atacccacct gtaagggaac    23280
ggagagggcc agggccttgg ctttctttca cttaatctca gttcaggtga ggacgcccag    23340
tctggctgct ccctctagca gcctgttcat tcatggcagc ccagctctct gcagggccct    23400
caggtgccca ggaaggaaag ctcctcccgc agccttgctc taggagccca gaacagggga    23460
gctggggcct ccgtgtgcca aagcttggac atggatgacc tcatctcctt ccttccttcc    23520
agcctgaggt gacttttttag agtccaggga tagctttcct caggcctgag ccaagaggag    23580
gtgtcattta acacaaggca gccagggagc ctgaagggag ttgaggacat ttatttcaca    23640
ttcacacaac tgtacatttt ctataaataa tgtggggctg aaatatttac agtcatttct    23700
tgcccatacc caggctgtct ctccctcctg acaccccgtg cctggagaga cagcctgcag    23760
acagatgtgc aaacccagct tggtctttcc tgcccctcc ctgatgctca ggcagagcag     23820
ccagcggtcc ctgggactcc actagcctcg accactccat cctctgatgc cgaaagcgtg    23880
gcaggccaca gggaattcgc cgctccactg cagtcacaga ngctgtggca ggcagcagcc    23940
aacactgcgg gcctgggcag tactgcggct tgggaatgca naagaagcag gaggtgcact    24000
cactcggctg ccccaatctc cttcctctct gtgcctctct gagaggtgag ccaggtctca    24060
ctctca                                                              24066
```